US008779115B2

(12) United States Patent
Ge et al.

(10) Patent No.: US 8,779,115 B2
(45) Date of Patent: Jul. 15, 2014

(54) SHORT HAIRPIN RNAS FOR INHIBITION OF GENE EXPRESSION

(75) Inventors: Qing Ge, Beijing (CN); Brian H. Johnston, Scotts Valley, CA (US); Sergei A Kazakov, San Jose, CA (US); Heini Ilves, Santa Cruz, CA (US); Anne Dallas, Santa Cruz, CA (US)

(73) Assignee: Somagenics Inc., Santa Cruz, CA (US)

( * ) Notice: Subject to any disclaimer, the term of this patent is extended or adjusted under 35 U.S.C. 154(b) by 0 days.

(21) Appl. No.: 13/591,433

(22) Filed: Aug. 22, 2012

(65) Prior Publication Data
US 2012/0329857 A1 Dec. 27, 2012

Related U.S. Application Data

(63) Continuation of application No. 12/579,323, filed on Oct. 14, 2009, now Pat. No. 8,283,460.

(60) Provisional application No. 61/105,606, filed on Oct. 15, 2008.

(51) Int. Cl.
C07H 21/04 (2006.01)

(52) U.S. Cl.
USPC .......................................................... 536/24.5

(58) Field of Classification Search
USPC .......................................................... 536/24.5
See application file for complete search history.

(56) References Cited

U.S. PATENT DOCUMENTS

| 6,001,990 | A | 12/1999 | Wands et al. | |
|---|---|---|---|---|
| 6,174,868 | B1 | 1/2001 | Anderson et al. | |
| 8,283,460 | B2 | 10/2012 | Ge et al. | |
| 2002/0156261 | A1 | 10/2002 | Malvy et al. | |
| 2003/0143732 | A1 | 7/2003 | Fosnaugh et al. | |
| 2003/0175772 | A1 | 9/2003 | Wang | |
| 2004/0053875 | A1 | 3/2004 | Kreutzer et al. | |
| 2004/0053876 | A1 | 3/2004 | Turner et al. | |
| 2004/0058886 | A1 | 3/2004 | Scaringe | |
| 2004/0138163 | A1* | 7/2004 | McSwiggen et al. | 514/44 |
| 2004/0209831 | A1 | 10/2004 | McSwiggen et al. | |
| 2004/0259247 | A1 | 12/2004 | Tuschi et al. | |
| 2005/0130919 | A1* | 6/2005 | Xu et al. | 514/44 |
| 2005/0164210 | A1 | 7/2005 | Mittal et al. | |
| 2005/0186586 | A1 | 8/2005 | Zamore et al. | |
| 2006/0134787 | A1 | 6/2006 | Zamore et al. | |
| 2006/0142228 | A1 | 6/2006 | Ford et al. | |
| 2006/0223777 | A1 | 10/2006 | Vermeulen et al. | |
| 2006/0293272 | A1 | 12/2006 | McSwiggen et al. | |
| 2007/0048759 | A1 | 3/2007 | Luo et al. | |
| 2007/0149470 | A1 | 6/2007 | Kaspar et al. | |
| 2007/0259827 | A1* | 11/2007 | Aronin et al. | 514/44 |
| 2009/0004739 | A1 | 1/2009 | Demura et al. | |
| 2009/0005332 | A1 | 1/2009 | Hauser et al. | |
| 2009/0035784 | A1* | 2/2009 | Ioannou et al. | 435/7.1 |
| 2009/0182136 | A1 | 7/2009 | Wengel et al. | |
| 2010/0112686 | A1 | 5/2010 | Ge et al. | |
| 2011/0269816 | A1* | 11/2011 | Kaspar et al. | 514/44 A |

FOREIGN PATENT DOCUMENTS

| WO | WO 03/070750 A2 | 8/2003 |
|---|---|---|
| WO | WO 03/070750 A3 | 3/2004 |
| WO | WO 2004/029281 A2 | 4/2004 |
| WO | WO 2005/028646 A1 | 3/2005 |
| WO | WO 2004/029281 A3 | 5/2005 |
| WO | WO 2005/079533 A2 | 9/2005 |
| WO | WO 2006/031901 A2 | 3/2006 |
| WO | WO 2006/078414 A2 | 7/2006 |
| WO | WO 2006/031901 A3 | 9/2006 |
| WO | WO 2007/032794 A2 | 3/2007 |
| WO | WO 2009/029688 A2 | 3/2009 |
| WO | WO 2009/078685 A2 | 6/2009 |

OTHER PUBLICATIONS

Birmingham et al., "3 UTR Seed Matches, but Not Overall Identity are Associated with RNAi Off-Targets"; Nature Methods, 3(3): 199-204 (2006); Addendum: Nature Methods, 3(6): 487 (2006).
Blight et al., "Efficient Initiation of HCV RNA Replication in Cell Culture"; Science, 290:1972-1974 (2000).
Bridge et al., "Induction of an Interferon Response by RNAi Vectors in Mammalian Cells"; Nature Genetics, 34(3): 263-264 (2003).
Brown et al., "Secondary Structure of the 5' Nontranslated Regions of Hepatitis C Virus and Pestivirus Genomic RNAs"; Nucleic Acids Research, 20(19): 5041-5045 (1992).
Bukh at al., "Sequence Analysis of the 5' Noncoding Regioon of Hepatitis C Virus"; Proc. Nat. Acad. Sci. USA 89:4942-4946 (1992).
Chinese Patent Application No. 200980149189.8 Office Action dated Mar. 5, 2013.
Choo et al., "Genetic Organization and Diversity of the Hepatitis C Virus"; Proc. Natl. Acad. Sci. USA, 88:2451-2455 (1991).
European Patent Application No. 9821213.7 Extended European Search Report dated Mar. 12, 2013.
Fish et al., "Short-Term Cytotoxic Effects and Long-Term Instability of RNAi Delivered Using Lentiviral Vectors"; BMC Molecular biology, 5:9 (2004).
Grimm et al., "Fatality in Mice Due to Oversaturation of Cellular MicroRNA/Short Hairpin RNA Pathways"; Nature, 441: 537-541 (2006).
Han et al., "Characterization of the Terminal Regions of the Hepatitis C Viral RNA: Identification of Conserved Sequences in the 5' Untranslated Region and Poly(A) Tails at the 3' End"; Proc. Natl. Acad. Sci. USA, 88: 1711-1715 (1991).
Hannon et al., "Unlocking the Potential of the Human Genome with RNA Interference"; Nature, 451: 371-378 (2004).
Harborth et al., "Sequence, Chemical, and Structural Variation of Small Interfering RNAs and Short Hairpin RNAs and the Effect on Mammalian Gene Silencing" Antisense and Nucleic Acid Drug Development (2003) 13:83-105.
Hugle et al., "Current Therapy and New Molecular Approaches to Antiviral Treatment and Prevention of Hepatitis C"; Rev. Med. Virol. 12: 361-371 (2003).

(Continued)

Primary Examiner — Brian Whiteman
(74) Attorney, Agent, or Firm — Wilson Sonsini Goodrich & Rosati

(57) ABSTRACT

Methods, compositions, and kits that include small hairpin RNA (shRNA) useful for inhibition of gene expression, such as viral-mediated gene expression, are described.

18 Claims, 14 Drawing Sheets

(56) References Cited

OTHER PUBLICATIONS

Ilves et al., "Inhibition of Hepatitis C IRES-Mediated Gene Expression by Small Hairpin RNAs in Human Hepatocytes and Mice"; Annals of the New York Academy of Sciences, vol. 1082, Oct. 2006, pp. 52-55.
International Search Report, corresponding to PCT1US2006 1021253, mailed Jun. 28, 2007 (3 pgs).
Jubin et al., "Hepatitis C Virus Internal Ribosome Entry Site (IRES) Stem Loop IIId Contains a Phylogenetically Conserved GGG Triplet Essential for Translation of IRES Folding"; Journal of Virology, 74(22): 10430-10437 (2000).
Kalota et al., "Design of antisense oligonucleotides an short interfering RNA duplexes (siRNA) targeted to BCL6 mRNA: Towards rational drug development for specific lymphoma subsets" (2007) Blood Cells, Molecules and Diseases 38:199-203.
Kapadia et al., "Interference of Hepatitis C Virus RNA Replication by Short Interfering RNAs"; Proc. Natl. Acad. Sci. USA 100(4): 2014-2018 (2003).
Kawasaki et al., "Short hairpin type of dsRNAs that are controlled by tRNAval promoter significantly induce RNAi¬ mediated gene silencing in the cytoplasm of human cells" Nucleic Acids Research (2003) 31(2):700-707.
Kawasaki et al., "Short Hairpin Type of dsRNAs that are Controlled by tRNAval Promoter Significantly Induce RNAi¬ meiated Gene Slicing in teh Cytoplasm of Human Cells"; Nucleic Acids Research; 31(2): 700-707 (2003).
Kim et al., Interferon Induction by siRNAs and ssRNAs Synthesized by Phage Polymerase:; Nature Biotechnology, 22 (3): 321-325 (2004).
Kronke et al., "Alternative Approaches for Efficient Inhibition of Hepatitis C Virus RNA Replication by Small Interfering RNAs"; Journal of Virology; 78(7) 3436-3446 (2004).
Lagos-Quintana et al., "Identification of Novel Genes Coding for Small Expressed RNAs"; Science, 294: 853-858 (2001).
Latham et al., "In RNA Interference Technology from Basic Science to Drug Development" Copyright (2005); Cambridge University Press, Chapter 10, pp. 153-154.
Layzer et al., "In Vivo Activity of Nuclease-Resistant siRNAs"; RNA, 10:776-771 (2004).
Li et al., "Defining the optimal parameters for hairpin-based knockdown constructs" RNA (2007) 23(2)L 227-231.
Lin et al., "Asymetry of Intronic Pre-miRNA Structures in Functional RISC Assembly." Gene, Elsevier, Amsterdam, NL, 356: 32-38 (2005).
Lieberman et al., "Interfering with Disease: Opportunities and Roadblocks to Harnessing RNA Interference"; Trends in Molecular Medicine; 9(9): 397-403 (2003).
Marques et al., "A Structural Basis for Discriminating Between Self and Nonself Double-Stranded RNAs in Mammalian Cells"; Nature Biotechnology, 24(5): 559-565 (2006).
McCaffrey et al., "A potent and specific morpholino antisense inhibitor of Hepatitis C translation in mice" Hepatology (2003) 38(2): 503-508.
McCaffrey et al., "Determinants of Hepatitis C Translational Initiation In Vitro, in Cultured Cells and Mice"; Molecular Therapy, 5(6): 676-684 (2002).
McCaffrey et al., "RNA Interference in Adult Mice"; Nature, 418:38-39 (2002).
McHutchison et al., "Future Therapy of Hepatitis C"; Hepatology, 36(5-S1): S245-S252 (2002).
McManus et al., "Gene silencing using micro-RNA designed hairpins" RNA (2002) 8: 842-850.
Mercer et al., "Hepatitis C Virus Replication in Mice with Chimeric Human Livers"; Nature Medicine, 7(8): 927-933 (2001).
Okamato et al., "Nucleotide Sequence of the Genomic RNA of Hepatitis C Virus Isolated from a Human Carrier: Comparison with Reported Isolates for Conserved and Divergent Regions"; J. Gen. Virol. 72(PT.11) 2697-2704 (1991) Abstract.
Paddison et al., "Short hairpin RNAs (shRNAs) induce sequence-specific silencing in mammalian cells" (2002) Genes & Dev. 16:948-958.
Pietschmann et al., "Tissue Culture an Animal Modes for Hepatitis C Virus"; Clinics in Liver Disease, 7:23-43 (2003).
Qin et al., "Inhibiting HIV-1 Infection in Human T Cells by Lentiviral-Mediated Delivery of Small Interfering RNA Against CCR5"; Proc. Natl. Acad. Sci. USA 100(1): 183-188 (2003).
Radhakrishnan et al., "RNA Interferences as a New Strategy Against Viral Hepatitis"; Virology, 323: 173-181 (2004).
Radharkrishnan et al., "RNA interference as a new strategy against viral hepatitis" Virology (2004) 323:173-181.
Randall et al., "Interfering with Hepatitis C Virus RNA Replication"; Virus Research, 102: 19-25 (2004).
Randall et al., "Clearance of Replicating Hepatitis C Virus Replicon RNAs in Cell Culture by Small Interfering RNAs"; Prof Natl. Acad. Sci. USA, 100(1): 235-240 (2003).
Rice, "Fresh Assault on Hepatitis C"; Nature, 426: 129-131 (2003).
Robbins et al., "Stable Expression of shRNAs in Human CD34+ Progenitor Cells can Avoid Induction of Interferon Responses to siRNAs In Vitro"; Nature Biotechnology, 24(5): 566-571 (2006).
Sano et al. "Effect of Asymmetric Terminal Structures of Short RNA Duplexes on the RNA Interference Activity and Strand Selection." Nucleic Acids Research,36 (18): 5812-5821 (2008).
Sen et al., "Inhibition of Hepatitis C Virus Protein Expression by RNA Interferences"; Virus Research, 96: 27-35 (2003).
Seo et al., "Letter to the Editor: Small Interfering RNA-Mediated Inhibition of Hepatitis C Virus Replication in the Human Hepatoma Cell Line Huh-7"; Journal of Virology, 77(1): 810-812 (2003).
Seyhan et al., "Complete, Gene-Specific siRNA Libraries: Production and Expression in Mammalian Cells"; RNA, 11(5): 837-846 (2005).
Simmonds et al.. "Identification of genotypes of hepatitis C virus by sequence comparisons in the core, El and NS-5 regions" (1994) J. Gen._ Virol. 75:1053-1061.
Siolas et al., "Synthetic shRNAs as potent RNAi triggers" Nature Biotechnology (2005) 23(2): 227-231.
Sookoian, "New Therapies on the Horizon for Hepatitis C"; Annals of Hepatology, 2(4): 164-170 (2003).
Vickers et al., "Efficient Reduction of Target RNAs by Small Interfering RNA and RNase H-dependent Antisense Agents" (2003), J. Biol. Chem 278: 7108-7118.
Vlassov et al., "shRNAs targeting hepatitis C: effects of sequence and structural features, and comparison with siRNA" Oligonucleotides (2007) 17:223-236.
Wang et al., "Small Hairpin RNAs Efficiently Inhibit Hepatitis C IRES-Mediated Gene Expression in Human Tissue Culture Cells and a Mouse Model" Molecular Therapy (Sep. 2005) 12(3):562-568.
Wang et al., "Small Hairpin RNAs Efficiently Inhibit Hepatitis C IRES-Mediated Gene Expression in Human Tissue Culture Cells and a Mouse Model"; Molecular Therapy, 12(3): 562-568 (2005).
Wilson et al., "RNA Interference Blocks Gene Expression and RNA Synthesis from Hepatitis C Replicons Propagated in Human Liver Cells"; Proc. Natl. Acad. Sci. USA, 100(5): 2783-2788 (2003).
Yokota et al., "Inhibition of intracellular hepatitis C virus replication by synthetic and vector derived small interfering RNAs" EMBO Reports (2003) 4(6):602-608.
Zhang et al., "Antisense Oligonucleotide Inhibition of Hepatitis C Virus (HCV) Gene Expression in Livers of Mice Infected with an HCV-Vaccinia Virus Recombinant"; Antimicrobial Agents and Chemotherapy, 43(2): 347-353 (1999).
Zhang et al., "Down-Regulation of Viral Replication by Adenoviral-Mediated Expression of siRNA Against Cellular Cofactors for Hepatitis C Virus"; Virology, 320: 135-143 (2004).

\* cited by examiner

```
                        SEQUENCE LISTING

<160> NUMBER OF SEQ ID NOS: 42

<210> SEQ ID NO 1
<211> LENGTH: 45
<212> TYPE: RNA
<213> ORGANISM: Artificial Sequence
<220> FEATURE:
<223> OTHER INFORMATION: Synthetic shRNA

<400> SEQUENCE: 1
gcacgaaucc uaaaccucac aauaugaggu uuaggauucg ugcuu              45

<210> SEQ ID NO 2
<211> LENGTH: 45
<212> TYPE: RNA
<213> ORGANISM: Artificial Sequence
<220> FEATURE:
<223> OTHER INFORMATION: Synthetic shRNA

<400> SEQUENCE: 2
ugagguuuag gauucgugcc aauagcacga auccuaaacc ucauu              45

<210> SEQ ID NO 3
<211> LENGTH: 45
<212> TYPE: RNA
<213> ORGANISM: Artificial Sequence
<220> FEATURE:
<223> OTHER INFORMATION: Synthetic shRNA

<400> SEQUENCE: 3
gugcaccaug agcacgaauc aauaauucgu gcucauggug cacuu              45

<210> SEQ ID NO 4
<211> LENGTH: 45
<212> TYPE: RNA
<213> ORGANISM: Artificial Sequence
<220> FEATURE:
<223> OTHER INFORMATION: Synthetic shRNA

<400> SEQUENCE: 4
auucgugcuc auggugcacc aauagugcac caugagcacg aauuu              45

<210> SEQ ID NO 5
<211> LENGTH: 44
<212> TYPE: RNA
<213> ORGANISM: Artificial Sequence
<220> FEATURE:
<223> OTHER INFORMATION: Synthetic shRNA

<400> SEQUENCE: 5
```
cuaaaccuca aagaaaaaca auauuuuucu uugagguuua gguu                    44

<210> SEQ ID NO 6
<211> LENGTH: 45
<212> TYPE: RNA
<213> ORGANISM: Artificial Sequence
<220> FEATURE:
<223> OTHER INFORMATION: Synthetic shRNA

<400> SEQUENCE: 6
uuuuucuuug agguuuaggc aauaccuaaa ccucaaagaa aaauu                   45

<210> SEQ ID NO 7
<211> LENGTH: 50
<212> TYPE: RNA
<213> ORGANISM: Artificial Sequence
<220> FEATURE:
<223> OTHER INFORMATION: Synthetic shRNA

<400> SEQUENCE: 7
ugagguuuag gauucgugcc uuccugucag cacgaauccu aaaccucauu              50

<210> SEQ ID NO 8
<211> LENGTH: 42
<212> TYPE: RNA
<213> ORGANISM: Artificial Sequence
<220> FEATURE:
<223> OTHER INFORMATION: Synthetic shRNA

<400> SEQUENCE: 8
ugagguuuag gauucgugcu ugcacgaauc cuaaaccuca uu                      42

<210> SEQ ID NO 9
<211> LENGTH: 41
<212> TYPE: RNA
<213> ORGANISM: Artificial Sequence
<220> FEATURE:
<223> OTHER INFORMATION: Synthetic shRNA

<400> SEQUENCE: 9
ugagguuuag gauucgugcu gcacgaaucc uaaaccucau u                       41

<210> SEQ ID NO 10
<211> LENGTH: 42
<212> TYPE: RNA
<213> ORGANISM: Artificial Sequence
<220> FEATURE:
<223> OTHER INFORMATION: Synthetic shRNA

<400> SEQUENCE: 10
auucgugcuc auggugcacu ugugcaccau gagcacgaau uu                      42

<210> SEQ ID NO 11
<211> LENGTH: 42
<212> TYPE: RNA
<213> ORGANISM: Artificial Sequence
<220> FEATURE:
<223> OTHER INFORMATION: Synthetic shRNA

<400> SEQUENCE: 11
gugcaccaug agcacgaauu uauucgugcu cauggugcac uu                      42

<210> SEQ ID NO 12
<211> LENGTH: 42
<212> TYPE: DNA

```
<213> ORGANISM: Artificial Sequence
<220> FEATURE:
<223> OTHER INFORMATION: Synthetic shRNA

<400> SEQUENCE: 12
ugagguuuag gauucgugct tgcacgaauc cuaaaccuca uu                    42

<210> SEQ ID NO 13
<211> LENGTH: 40
<212> TYPE: RNA
<213> ORGANISM: Artificial Sequence
<220> FEATURE:
<223> OTHER INFORMATION: Synthetic shRNA

<400> SEQUENCE: 13
ugagguuuag gauucgugcu ugcacgaauc cuaaaccuca                       40

<210> SEQ ID NO 14
<211> LENGTH: 42
<212> TYPE: DNA
<213> ORGANISM: Artificial Sequence
<220> FEATURE:
<223> OTHER INFORMATION: Synthetic shRNA

<400> SEQUENCE: 14
ugagguuuag gauucgugcu ugcacgaauc cuaaaccuca tt                    42

<210> SEQ ID NO 15
<211> LENGTH: 38
<212> TYPE: RNA
<213> ORGANISM: Artificial Sequence
<220> FEATURE:
<223> OTHER INFORMATION: Synthetic shRNA

<400> SEQUENCE: 15
ugagguuuag gauucgugcu ugcacgaauc cuaaaccu                         38

<210> SEQ ID NO 16
<211> LENGTH: 37
<212> TYPE: RNA
<213> ORGANISM: Artificial Sequence
<220> FEATURE:
<223> OTHER INFORMATION: Synthetic shRNA

<400> SEQUENCE: 16
ugagguuuag gauucgugcu ugcacgaauc cuaaacc                          37

<210> SEQ ID NO 17
<211> LENGTH: 38
<212> TYPE: RNA
<213> ORGANISM: Artificial Sequence
<220> FEATURE:
<223> OTHER INFORMATION: Synthetic shRNA

<400> SEQUENCE: 17
ugagguuuag gauucguguu cacgaauccu aaaccuca                         38

<210> SEQ ID NO 18
<211> LENGTH: 36
<212> TYPE: RNA
<213> ORGANISM: Artificial Sequence
<220> FEATURE:
<223> OTHER INFORMATION: Synthetic shRNA

<400> SEQUENCE: 18
ugagguuuag gauucgugca cgaauccuaa accuca                           36
```

<210> SEQ ID NO 19
<211> LENGTH: 30
<212> TYPE: RNA
<213> ORGANISM: Artificial Sequence
<220> FEATURE:
<223> OTHER INFORMATION: Synthetic shRNA

<400> SEQUENCE: 19
ugagguuuag gauucgugcc cuaaaccuca                                    30

<210> SEQ ID NO 20
<211> LENGTH: 42
<212> TYPE: RNA
<213> ORGANISM: Artificial Sequence
<220> FEATURE:
<223> OTHER INFORMATION: Synthetic shRNA

<400> SEQUENCE: 20
ugagguuuag gauucgugcu ugcacguauc cuaaaccuca uu                      42

<210> SEQ ID NO 21
<211> LENGTH: 34
<212> TYPE: RNA
<213> ORGANISM: Artificial Sequence
<220> FEATURE:
<223> OTHER INFORMATION: Synthetic shRNA

<400> SEQUENCE: 21
ugagguuuag gauucguucg aauccuaaac cuca                               34

<210> SEQ ID NO 22
<211> LENGTH: 32
<212> TYPE: RNA
<213> ORGANISM: Artificial Sequence
<220> FEATURE:
<223> OTHER INFORMATION: Synthetic shRNA

<400> SEQUENCE: 22
ugagguuuag gauucuugaa uccuaaaccu ca                                 32

<210> SEQ ID NO 23
<211> LENGTH: 29
<212> TYPE: RNA
<213> ORGANISM: Artificial Sequence
<220> FEATURE:
<223> OTHER INFORMATION: Synthetic shRNA

<400> SEQUENCE: 23
ugagguuuag gauucgugac uaaaccuca                                     29

<210> SEQ ID NO 24
<211> LENGTH: 32
<212> TYPE: RNA
<213> ORGANISM: Artificial Sequence
<220> FEATURE:
<223> OTHER INFORMATION: Synthetic shRNA

<400> SEQUENCE: 24
ugagguuuag gauucgugca uccuaaaccu ca                                 32

<210> SEQ ID NO 25
<211> LENGTH: 30
<212> TYPE: RNA
<213> ORGANISM: Artificial Sequence
<220> FEATURE:

```
<223> OTHER INFORMATION: Synthetic shRNA

<400> SEQUENCE: 25
gcacgaaucc uugagguuua ggauucgugc                                    30

<210> SEQ ID NO 26
<211> LENGTH: 36
<212> TYPE: RNA
<213> ORGANISM: Artificial Sequence
<220> FEATURE:
<223> OTHER INFORMATION: Synthetic shRNA

<400> SEQUENCE: 26
auucgugcuc auggugcacg caccaugagc acgaau                             36

<210> SEQ ID NO 27
<211> LENGTH: 40
<212> TYPE: RNA
<213> ORGANISM: Artificial Sequence
<220> FEATURE:
<223> OTHER INFORMATION: Synthetic shRNA

<400> SEQUENCE: 27
auucgugcuc auggugcacu ugugcaccau gagcacgaau                         40

<210> SEQ ID NO 28
<211> LENGTH: 42
<212> TYPE: RNA
<213> ORGANISM: Artificial Sequence
<220> FEATURE:
<223> OTHER INFORMATION: Synthetic shRNA

<400> SEQUENCE: 28
uuuuucuuug agguuuaggu uccuaaaccu caaagaaaaa uu                      42

<210> SEQ ID NO 29
<211> LENGTH: 40
<212> TYPE: RNA
<213> ORGANISM: Artificial Sequence
<220> FEATURE:
<223> OTHER INFORMATION: Synthetic shRNA

<400> SEQUENCE: 29
uuuuucuuug agguuuaggu uccuaaaccu caaagaaaaa                         40

<210> SEQ ID NO 30
<211> LENGTH: 40
<212> TYPE: RNA
<213> ORGANISM: Artificial Sequence
<220> FEATURE:
<223> OTHER INFORMATION: Synthetic shRNA

<400> SEQUENCE: 30
uuuuucuuug agguuuaguu cuaaaccuca aagaaaaauu                         40

<210> SEQ ID NO 31
<211> LENGTH: 42
<212> TYPE: RNA
<213> ORGANISM: Artificial Sequence
<220> FEATURE:
<223> OTHER INFORMATION: Synthetic shRNA

<400> SEQUENCE: 31
ugagguuuag gauucgugcu ugcacgcauc cuaaaccuca uu                      42
```

<210> SEQ ID NO 32
<211> LENGTH: 42
<212> TYPE: RNA
<213> ORGANISM: Artificial Sequence
<220> FEATURE:
<223> OTHER INFORMATION: Synthetic shRNA

<400> SEQUENCE: 32
ugagguuuag gauucgugcu ugcacgacuc cuaaaccuca uu                         42

<210> SEQ ID NO 33
<211> LENGTH: 42
<212> TYPE: RNA
<213> ORGANISM: Artificial Sequence
<220> FEATURE:
<223> OTHER INFORMATION: Synthetic shRNA

<400> SEQUENCE: 33
ugagguuuag gauucgugcu ugcaccaauc cuaaaccuca uu                         42

<210> SEQ ID NO 34
<211> LENGTH: 42
<212> TYPE: RNA
<213> ORGANISM: Artificial Sequence
<220> FEATURE:
<223> OTHER INFORMATION: Synthetic shRNA

<400> SEQUENCE: 34
ugagguuuag gauucgugcu ugcaggaauc cuaaaccuca uu                         42

<210> SEQ ID NO 35
<211> LENGTH: 28
<212> TYPE: RNA
<213> ORGANISM: Artificial Sequence
<220> FEATURE:
<223> OTHER INFORMATION: Synthetic shRNA

<400> SEQUENCE: 35
ugagguuuag gauucgugcc aauagcac                                         28

<210> SEQ ID NO 36
<211> LENGTH: 17
<212> TYPE: RNA
<213> ORGANISM: Artificial Sequence
<220> FEATURE:
<223> OTHER INFORMATION: Synthetic shRNA

<400> SEQUENCE: 36
gaauccuaaa ccucauu                                                     17

<210> SEQ ID NO 37
<211> LENGTH: 30
<212> TYPE: RNA
<213> ORGANISM: Artificial Sequence
<220> FEATURE:
<223> OTHER INFORMATION: Synthetic shRNA

<400> SEQUENCE: 37
gcacgaaucc uaaaccucaa agcaugcucc                                       30

<210> SEQ ID NO 38
<211> LENGTH: 32
<212> TYPE: RNA
<213> ORGANISM: Artificial Sequence
<220> FEATURE:
<223> OTHER INFORMATION: Synthetic shRNA

```
<400> SEQUENCE: 38
accguggucu uugagguuua ggauucgugc uu                          32

<210> SEQ ID NO 39
<211> LENGTH: 16
<212> TYPE: RNA
<213> ORGANISM: Artificial Sequence
<220> FEATURE:
<223> OTHER INFORMATION: Synthetic shRNA

<400> SEQUENCE: 39
ggagcaugac cacggu                                            16

<210> SEQ ID NO 40
<211> LENGTH: 64
<212> TYPE: RNA
<213> ORGANISM: Artificial Sequence
<220> FEATURE:
<223> OTHER INFORMATION: Synthetic shRNA

<400> SEQUENCE: 40
gggagcacga auccuaaacc ucaaagacuu ccugucaucu uugagguuua ggauucgugc    60
ucuu                                                         64

<210> SEQ ID NO 41
<211> LENGTH: 10
<212> TYPE: RNA
<213> ORGANISM: Artificial Sequence
<220> FEATURE:
<223> OTHER INFORMATION: Synthetic RNA

<400> SEQUENCE: 41
cuuccuguca                                                   10

<210> SEQ ID NO 42
<211> LENGTH: 45
<212> TYPE: RNA
<213> ORGANISM: Artificial Sequence
<220> FEATURE:
<223> OTHER INFORMATION: Synthetic RNA

<400> SEQUENCE: 42
cgugcuuagg auuuggaguc aauaacucca aauccuaagc acguu            45
```

SHORT HAIRPIN RNAS FOR INHIBITION OF GENE EXPRESSION

This application is a continuation of U.S. application Ser. No. 12/579,323, now U.S. Pat. No. 8,283,460 entitled "SHORT HAIRPIN RNAS FOR INHIBITION OF GENE EXPRESSION" filed Oct. 14, 2009; which claims the benefit of U.S. provisional application Ser. No. 61/105,606, filed Oct. 15, 2008, the entirety of both of which are incorporated herein by reference.

STATEMENT REGARDING FEDERALLY SPONSORED RESEARCH OF DEVELOPMENT

This invention was made in part during work supported by NIH grant R44AI056611 (BHJ) from the National Institutes of Health. The government may have certain rights in the invention.

SEQUENCE LISTING

The instant application contains a Sequence Listing which has been submitted in ASCII format via EFS-Web and is hereby incorporated by reference in its entirety. Said ASCII copy, created on Mar. 25, 2014, is named 40220-703-301-Updated-SeqListing.txt and is 8 Kilobytes in size.

FIELD OF THE INVENTION

The invention relates to inhibition of viral gene expression, for example, hepatitis C IRES-mediated gene expression, with short hairpin RNA (shRNA).

BACKGROUND OF THE INVENTION

RNA interference (RNAi) is a cellular process that uses double stranded RNA (dsRNA) to target messenger RNA (mRNAs) for degradation and translation attenuation. The process is gene specific, refractory to small changes in target sequence, and amenable to multigene targeting. This phenomenon was first reported in plants in 1990 (Napoli, C., et al., Introduction of a chimeric chalcone synthase gene into petunia results in reversible co-suppression of homologous genes in trans. Plant Cell, 1990, 2(4):279-289). It was later observed in other organisms including fungi and worms (Romano, N., et al., Quelling: transient inactivation of gene expression in *Neurospora crassa* by transformation with homologous sequences. Mol. Microbiol., 1992, 6(22):3343-53). Mechanistically, long dsRNA can be cleaved into short interfering RNA (siRNA) duplexes by Dicer, a Type III RNase. Subsequently, these small duplexes interact with the RNA Induced Silencing Complex (RISC), a multisubunit complex that contains both helicases and endonuclease activities that mediate degradation of homologous transcripts. The discovery that synthetic siRNAs of ~19-29 bp can effectively inhibit gene expression in mammalian cells and animals has led to a flurry of activity to develop these inhibitors as therapeutics (Elbashir, S. M., et al., Duplexes of 21-nucleotide RNAs mediate RNA interference in cultured mammalian cells. Nature, 2001, 411(6836):494-8). Recent development of advanced siRNA selection methods, including algorithm-based rational design selection, allows the researchers to select potent siRNA duplexes by key sequence and thermodynamic parameters that are target sequence independent (Khvorova, A., et al., Functional siRNAs and miRNAs exhibit strand bias. Cell, 2003, 115(1):209-216).

Small hairpin RNAs (shRNA) of 19-29 bp that are chemically synthesized or expressed from bacteriophage (e.g., T7, T3 or SP6) or mammalian (pol III such as U6 or H1 or pol II) promoters have also shown robust inhibition of target genes in mammalian cells. Furthermore, synthetic shRNA with its unimolecular structure has advantages in potency and simplicity over two-strand-comprising siRNA, the latter requiring the careful annealing of exact stoichiometric amounts of two separate strand which may have different purity profiles and off-target effects (Siolas, D., et al., Synthetic shRNAs as potent RNAi triggers. Nature Biotechnology, 2005, 23(2):227-231; Vlassov, A. V., et al., shRNAs targeting hepatitis C: effects of sequence and structural features, and comparison with siRNA. Oligonucleotides, 2007, 17:223-236).

However, a number of challenges have arisen over the course of shRNA design and development. First, researchers have observed wide-ranging variability in the level of silencing induced by different shRNA. Second, shRNA that varies in stem length, loop length and loop position has different knockdown capability (McManus, M. T., et al., Gene silencing using micro-RNA designed hairpins. RNA, 2002, 8:842-850; Harborth, J., et al., Sequence, chemical, and structural variatioin of small interfering RNAs and short hairpin RNAs and the effect on mammalian gene silencing. Antisense And Nucleic Acid Drug Development. 2003, 13:83-105; Li, L., et al., Defining the optimal parameters for hairpin-based knockdown constructs. RNA, 2007, 13:1765-1774; Vlassov, A. V., et al., shRNAs targeting hepatitis C: effects of sequence and structural features, and comparison with siRNA. Oligonucleotides, 2007, 17:223-236). Some shRNAs having a 19-nucleotide guide strand at the 5' end of the hairpin (left-hand loop) have been found to be more efficacious than those having their guide strand at the 3' end of the hairpin (right-hand loop) (Scaringe, S. US 2004/0058886 A1), while other shRNAs were reported to be more efficacious with the right-hand loop structure (Vermeulen, et al. US 2006/0223777 A1). shRNAs with a 19-mer guide strand at the 3' end of the hairpin (right-hand loop) were found to be more potent than 25- or 29-mer shRNAs (with right-hand loop). Previously available limited data suggested that the optimal loop size for a shRNA with a 19-bp stem with right-hand loop is larger than 4 nucleotides and preferably 9 or 10 nucleotides. A third challenge is that the mechanism of processing in the cytoplasm of synthetic shRNAs, especially 19-mer hairpins, is unknown. Unlike long dsRNAs and 29-mer shRNAs, 19-mer shRNAs are not cleaved by Dicer (Siolas, D., et al., Synthetic shRNAs as potent RNAi triggers. Nature Biotechnology, 2005, 23(2):227-231). Therefore, it would be advantageous to have a reliable design for superior shRNAs and a better understanding of the structure-activity relationship and processing of shRNAs to provide highly functional inhibitors.

SUMMARY OF THE INVENTION

The present invention is directed to methods and compositions pertaining to shRNA, fractured shRNA, and T-shaped RNA for use in gene silencing. Accordingly, the present invention provides compositions, methods, and kits for increasing the efficiency of RNA interference.

In one aspect, the invention features a polynucleotide, e.g., a DNA or an RNA molecule, comprising a first sequence (e.g., a first RNA sequence), e.g., a guide strand, consisting of 15 nucleotides to 30 nucleotides, wherein the first sequence is at least partially complementary to a target nucleotide sequence; a second sequence (e.g., a second RNA sequence), e.g., a passenger strand, comprising a sequence that is at least partially complementary to at least a portion of the first sequence, the second sequence having a length of between 10 nucleotides and 1 fewer nucleotide than the length of the first sequence; optionally a loop sequence positioned between the first sequence and the second sequence, the loop consisting of 1 to 100 nucleotides; and optionally a nucleotide overhang consisting of 1 to 2 nucleotides.

In another aspect, the invention features a polynucleotide, e.g., a DNA or an RNA molecule, comprising a first sequence (e.g., a first RNA sequence), e.g., a guide strand, consisting of 16 nucleotides to 30 nucleotides, wherein the first sequence is at least partially complementary to a target nucleotide sequence; a second sequence (e.g., a second RNA sequence), e.g., a passenger strand, comprising a sequence that is at least partially complementary to at least a portion of the first sequence, the second sequence having at least one more nucleotide than the first sequence, and the second sequence having no more than 100 nucleotides; optionally a loop sequence positioned between the first sequence and the second sequence, the loop consisting of 1 to 100 nucleotides; and optionally a nucleotide overhang consisting of 1 to 2 nucleotides.

In another aspect, the invention features a polynucleotide, e.g., a DNA or an RNA molecule, comprising a first sequence (e.g., a first RNA sequence), e.g., a guide strand, consisting of 16 nucleotides to 18 nucleotides, wherein the first sequence is at least partially complementary to a target nucleotide sequence; a second sequence (e.g., a second RNA sequence), e.g., a passenger strand, comprising a sequence that is at least partially complementary to at least a portion of the first sequence, the second sequence having the same number of nucleotides as the first sequence; optionally a loop sequence positioned between the first sequence and the second sequence, the loop consisting of 1 to 2 nucleotides; and optionally a nucleotide overhang consisting of 1 to 2 nucleotides.

In another aspect, the invention features a polynucleotide, e.g., a DNA or an RNA molecule, comprising a first sequence (e.g., a first RNA sequence), e.g., a guide strand, consisting of 19 nucleotides, wherein the first sequence is at least partially complementary to a target nucleotide sequence; a second sequence (e.g., a second RNA sequence), e.g., a passenger strand, comprising a sequence that is at least partially complementary to at least a portion of the first sequence, the second sequence consisting of 17 nucleotides or 18 nucleotides; optionally a loop sequence positioned between the first sequence and the second sequence, the loop consisting of 1 to 100 nucleotides; and optionally a nucleotide overhang consisting of 1 to 2 nucleotides.

In another aspect, the invention features a polynucleotide, e.g., a DNA or an RNA molecule, comprising a first sequence (e.g., a first RNA sequence), e.g., a guide strand, consisting of 15 nucleotides to 30 nucleotides, wherein the first sequence is at least partially complementary to a target nucleotide sequence; a second sequence (e.g., a second RNA sequence), e.g., a passenger strand, comprising a sequence that is at least partially complementary to at least a portion of the first sequence, the second sequence having the same or fewer number of nucleotides as the first sequence; optionally a loop sequence positioned between the first sequence and the second sequence, the loop consisting of 1 nucleotide; and optionally a nucleotide overhang consisting of 1 to 2 nucleotides.

In another aspect, the invention features an RNA molecule comprising a first RNA sequence, e.g., a guide strand, consisting of about 5 nucleotides to about 15 nucleotides, wherein the first sequence is at least partially complementary to a target nucleotide sequence; a second RNA sequence, e.g., a passenger strand, capable of forming a hairpin structure with the first sequence, the hairpin structure comprising from about 23 nucleotides to about 100 nucleotides, and the second sequence comprising: a first region having at least 80% complementarity with the first sequence and being capable of forming a first duplex region of fewer than 19 base pairs with the first sequence; a second region coupled to the first region; a third region coupled to the second region; and a fourth region coupled to the third region and having at least 80% complementarity with the second region, the fourth region being capable of forming a second duplex region with the second region such that the third region forms a loop adjacent to the second duplex region and the sum of the lengths of the first duplex region and the second duplex region is less than 23 base pairs; and optionally, an overhang on the 5' or 3' end of the RNA molecule of fewer than about 6 nucleotides.

In another aspect, the invention features an RNA molecule comprising an RNA sequence of any one of SEQ ID NOs: 1-39.

In some embodiments, the third region forms a loop that includes nucleotides having the sequence of 5'-UU-3'. Further, the second strand can include a part of passenger strand with a 5' phosphate group. In one embodiment, the second strand with the 5' phosphate group is adjacent to the fourth region of the second strand. In another embodiment, the second strand with the 5' phosphate group is not adjacent to the fourth region of the second strand.

In another aspect, the invention features a T-shaped RNA molecule, comprising a first RNA sequence, e.g., a guide strand, that is at least partially complementary to a target nucleotide sequence, a second RNA sequence, e.g., a passenger strand, and a third RNA sequence, wherein the first sequence comprises a first region having from about 18 nucleotides to about 29 nucleotides at least 80% complementary to a first region of the second sequence; the first sequence further comprises a second region having about 4 nucleotides to about 10 nucleotides at least about 90% complementary to a first region of the third sequence; the second sequence comprises a first region having from about 18 nucleotides to about 29 nucleotides at least about 80% complementary to the first region of the first sequence; the second sequence further comprises a second region having about 4 nucleotides to about 10 nucleotides at least about 90% complementary to a second region of the third sequence, wherein the second region of the third sequence is 3' adjacent to the first region of the third sequence; and optionally, an overhang on the 5' or 3' end of the RNA molecule of fewer than about 6 nucleotides.

In some embodiments of any of the aspects described herein, a polynucleotide, e.g., a DNA or RNA molecule described herein, can include from about 30 nucleotides to about 84 nucleotides.

In some embodiments of any of the aspects described herein, a polynucleotide, e.g., a DNA or RNA molecule described herein, includes a second sequence that comprises a sequence that is at least about 80%, at least about 85%, at least about 90%, at least about 95%, at least about 96%, at least about 97%, at least about 98%, at least about 99%, or about 100% complementary to at least a portion of the first sequence. In particular embodiments, the second sequence comprises a sequence, e.g., at the 3' end of the second sequence, that is at least about 80%, at least about 85%, at least about 90%, at least about 95%, at least about 96%, at least about 97%, at least about 98%, at least about 99%, or about 100% complementary to a portion at the 5' end of the first sequence.

In some embodiments of any of the aspects described herein, a polynucleotide, e.g., a DNA or RNA molecule described herein, includes at least one modification, e.g., chemical modification described herein. In some embodiments, about 20% to about 100%, e.g., about 40% to about 90%, of the nucleotides in an RNA molecule described herein are chemically modified. In one embodiment, about 20% to about 100% of the Us and Cs in an RNA molecule described herein are 2' O-methyl modified or 2' F.

In some embodiments of any of the aspects described herein, a polynucleotide, e.g., a DNA or RNA molecule described herein, includes a loop that includes at least one non-nucleotide molecule.

In some embodiments of any of the aspects described herein, a polynucleotide, e.g., a DNA or RNA molecule described herein, includes an overhang at the 3' end or the 5' end of the molecule. For example, the overhang is 1, 2, 3, 4, 5, 6, 7, 8, 9, or 10 nucleotides.

In some embodiments of any of the aspects described herein, a polynucleotide, e.g., a DNA or RNA molecule described herein, includes 1 or 2 mismatches between the first sequence and the second sequence. In one embodiment, a mismatch exists at position 11, 12, 13, 14, 15, 16, or 17 on the guide strand counting from the 5' end and the opposite nucleotide in the passenger strand, preferably at position 14 on the guide strand counting from the 5' end and the opposite nucleotide in the passenger strand.

In some embodiments of any of the aspects described herein, the first sequence is 3' to the second sequence. In other embodiments, the first sequence is 5' to the second sequence.

In some embodiments of any of the aspects described herein, an RNA molecule described herein further includes at least one conjugate moiety attached to the loop region or 3' terminus of the RNA molecule via a linker. The conjugate moiety can be a steroid molecule, a vitamin, a peptide, galactose and derivatives thereof, or a protein. In some embodiments, the conjugate moiety is a steroid molecule selected from the group consisting of cholesterol, cholestanol, stigmasterol, cholanic acid, and ergosterol. In other embodiments, the conjugate moiety is cholesterol, and the linker is a C5 linker molecule. In yet other embodiments, the conjugate moiety is vitamin E.

In other embodiments, an RNA molecule described herein further includes at least one detectable label attached to the loop region or 3' terminus of the RNA molecule. In some embodiments, the detectable label is a dye molecule. In some embodiments, the RNA molecule can include both a conjugate moiety and a detectable label.

In some embodiments, an RNA molecule described herein is capable of inhibiting expression of the target nucleotide sequence, e.g., a viral sequence. In some embodiments, the viral sequence is a hepatitis C viral sequence. In certain embodiments, the target nucleotide sequence is a sequence within the internal ribosome entry site (IRES) sequence of hepatitis C virus.

In another aspect, the invention features a DNA sequence comprising a sequence encoding an RNA molecule described herein, or an expression vector comprising a DNA sequence comprising a sequence encoding an RNA molecule described herein. In some embodiments, the vector is a retroviral vector.

In another aspect, the invention features a composition comprising an RNA molecule described herein, and a pharmaceutically acceptable excipient. In another aspect, the invention features a composition comprising a vector comprising a sequence encoding an RNA molecule described herein.

In another aspect, the invention features a method of inhibiting the expression or activity of a gene, the method comprising contacting a cell that expresses the gene with an RNA molecule described herein, wherein the first RNA sequence is at least partially complementary to a target nucleotide sequence encoded by at least a portion of the gene.

In another aspect, the invention features a method of inhibiting expression or activity of a hepatitis C virus, the method comprising contacting a cell that expresses a hepatitis C virus with an RNA molecule described herein, wherein the first RNA sequence is at least partially complementary to a hepatitis C viral sequence.

In any of these aspects, the cell can be in a mammal, e.g., a human or a non-human primate.

In certain embodiments, an RNA molecule described herein does not induce an IFN response.

In another aspect, the invention features a kit comprising a container, the container comprising an RNA molecule described herein; and optionally a reduced serum tissue culture medium.

The following figures are presented for the purpose of illustration only, and are not intended to be limiting.

BRIEF DESCRIPTION OF THE DRAWINGS

FIG. 4A compares the potency of shRNA with 10-, 5-, 2-, and 1-nucleotide (nt) loop. The sequences of the duplex regions are the same among these shRNAs and siRNA 19-3. The results indicate that shRNAs with 5'-guide strands have higher potencies when the loop size is very small (1- or 2-nt) than when it is larger (5- or 10-nt). The loop sequence likely doesn't affect the shRNA activity since three different loop sequences were used. FIG. 4B compares the activity of shRNAs with U:A and C:G base pairs immediately before the loop. The sequences of the loop (in underline) and the adjacent base pair are shown in parentheses. The sequence of the duplex region is the same among these shRNAs. The comparison indicates that when the loop is 2-nt in length, the shRNA having a C:G base pair adjacent to the loop gives better potency than that with an adjacent U:A pair. FIG. 4C shows that the UU-ribonucleotide sequence in the loop of shRNA can be replaced with a TT-deoxyribonucleotide sequence without affecting the efficacy of the shRNA. The sequence of the duplex is the same for both of these shRNAs and siRNA 19-3.

FIG. 5A compares the activity of shRNAs with and without 3' overhang. The result indicates that the shRNAs with blunt end or with 3'-TT overhang have very similar potency as the corresponding shRNA with 3'-UU overhang. FIG. 5B compares the potency of shRNA with various lengths of duplex or passenger strand. g/p values represent the lengths of guide strand/passenger strands. The comparison suggests that shortening passenger strand to 17- or 16-nt while maintaining the length of guide strand at 19-nt significantly reduces gene silencing activity (SG115 and SG116). However, shortening both passenger and guide strands to 18-nt in length did not have a significant impact on potency (SG117). FIG. 5C depicts the activity of shRNAs with even shorter duplex lengths. The shRNAs with 17 or 16 base pairs in the duplex (SG117 and SG119) have very similar efficacy. Although the shRNA with 11 base pairs in the duplex (SG120) shows a significant loss of silencing activity, the $IC_{50}$ of this molecule is still in the subnanomolar range.

FIG. 6A compares the activity of shRNAs varying lengths of both guide and passenger strands. The result shows that the potency of shRNAs decreases significantly when shRNAs with duplex lengths of 14-base pairs or less were used (SG132 and SG120). FIG. 6B depicts the activity of shRNAs with 10- to 13-nt passenger strands while maintaining the length of guide strand at 19-nt. The result indicates that the activity of shRNA requires the hairpin containing a minimum length of 11-nt for the passenger strand.

FIGS. 7A and 7B show the activity of shRNAs against the same target as si72 and si74, respectively, but differ in structures. The results indicate that 3'-UU overhang is not essential for the activity of shRNA. Shortening the duplex region could partially reduce the target gene knockdown activity.

FIG. 8A shows a similar activity between shRNA with (SG110) and without (SG142) a single mismatch at position 6 from 5' end of the passenger strand (opposite position 14 from 5' end of the guide strand). FIG. 8B shows a similar activity among shRNAs without (SG142) and with a single mismatch at position 6 (SG126), 7 (SG127), 5 (SG128), and 4 (SG129) from 5' end of the passenger strand respectively (opposite position 14, 13, 15 and 16 from 5' end of the guide strand). This lack of activity loss with single mismatch appears to be unrelated to the type of mismatch (e.g., U-U (SG110)=U-C (SG126)) suggesting that this trait is sequence independent. All the shRNAs have 5'-UU-3' loop and 3'-UU overhang.

FIG. 9A compares the target inhibition of shRNA with and without heating and snap-cooling. Although slightly lower than the shRNAs with multiple species, the single species of shRNA monomers obtained by heating and snap-cooling show high activity in target gene silencing irrespective of sequence or length tested. FIG. 9B shows the monomer, dimer and oligomer of shRNA in 10% naïve polyacrylamide gel with and without heating (95° C. for 4 minutes) and snap-cooling of shRNA in ice-water bath. The gel was stained with SYBR Gold (Invitrogen).

FIG. 10A shows that SG119 has higher silencing activity when majority is monomer whereas SG120 has higher silencing activity when majority is dimer. FIG. 10B shows the monomer, dimer and oligomer of shRNA in 10% naïve polyacrylamide gel with and without heating (95° C. for 4 minutes) and snap-cooling of shRNA in ice-water bath.

FIG. 13A depicts the expression of the IFN-responsive gene OAS1 in human peripheral blood mononuclear cells (PBMC) after shRNA transfection. FIG. 13B depicts the 3-(4,5-dimethylthiazol-2-yl)-2,5-diphenyltetrazolium bromide (MTT) incorporation in human hepatocarcinoma cell line (Huh7) after shRNA transfection. Together, these panels of FIGS. 13A and 13B indicate that no IFN response or cytotoxicity were induced by these shRNAs.

DETAILED DESCRIPTION OF THE INVENTION

Figure 1:
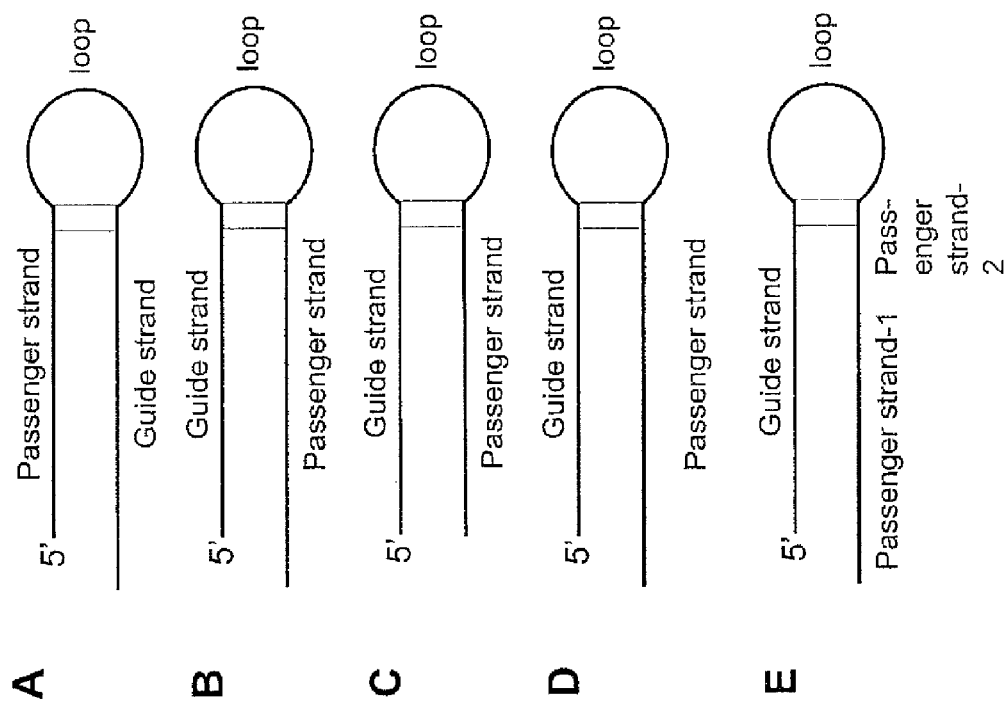
FIGS. 1A-1D depict the structure of embodiments of hairpin containing various configurations.
Figure 2:
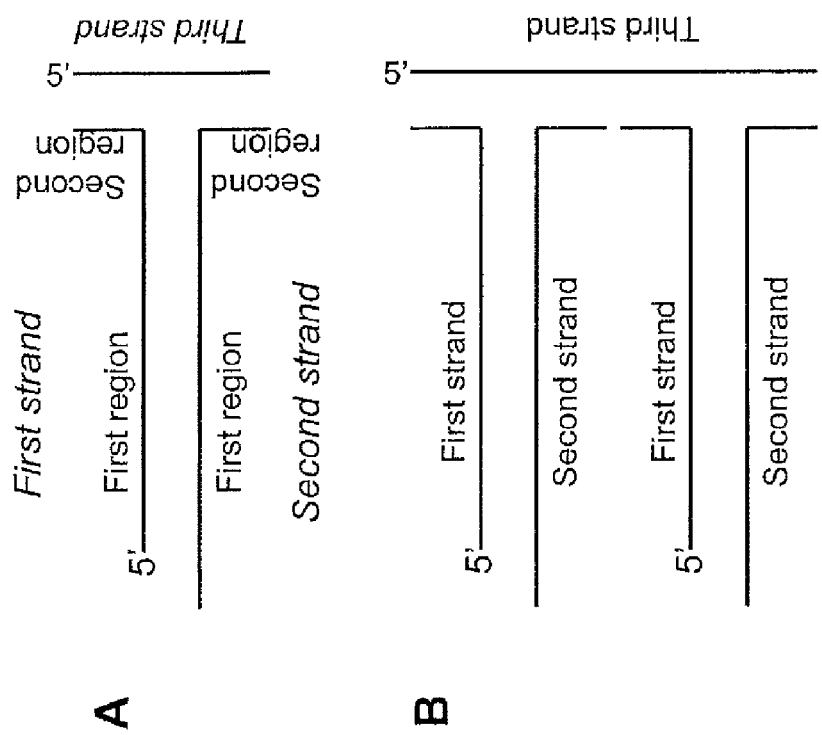
FIG. 2 depicts the structure of T-shaped RNA molecule and multiplication of T-shaped RNA molecule by having a long third strand with repeated sequence complementary to the second region of first and second strands.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein, including GenBank database sequences, are incorporated by reference in their entirety. In case of conflict, the present specification, including definitions, will control. In addition, the materials, methods, and examples are illustrative only and not intended to be limiting.

Embodiments of the present disclosure are directed to compositions and methods for performing shRNA-induced gene silencing. Through the use of shRNA, modified shRNA, fractured shRNA, modified fractured shRNA, T-shaped RNA and derivatives thereof, the efficiency of RNA interference may be improved. Accordingly, the present disclosure provides compositions, methods, and kits for increasing the functionality of shRNA. Preferably, the disclosure provides compositions and methods for improving the functionality of shRNA for inhibiting viral gene expression and/or treating a viral infection in a mammal, such as a human. In some embodiments, the shRNA constructs described herein inhibit gene expression of a virus by inducing cleavage of viral polynucleotide sequences within or near the target sequence that is recognized by the guide strand sequence of the shRNA.

The phrase "short hairpin RNA" and the term "shRNA", as used herein, refer to a unimolecular RNA that is capable of performing RNAi and that has a passenger strand, a loop, and a guide strand. Preferably, the passenger and guide strands are substantially complementary to each other. The guide strand can be about 16 to about 29 nucleotides in length, and more preferably 18 to 19 nucleotides in length. The passenger strand can be about 11 to about 29 nucleotides in length, and more preferably 17 to 19 nucleotides in length. The guide strand can contain at least 17 bases that are complementary to a target mRNA. In some embodiments, the guide strand that is complementary to the target can contain mismatches. The sequence can be varied to target one or more genetic variants or phenotypes of a target, e.g., a viral target, by altering the targeting sequence to be complementary to the sequence of the genetic variant or phenotype. In some embodiments, a sequence can target multiple viral strains, e.g., of HCV, although the sequence can differ from the target of a strain by at least one nucleotide (e.g., one, two, or three nucleotides) of a targeting sequence. An shRNA may have a loop as long as, for example, 0 to about 24 nucleotides in length, preferably 0 to about 10 nucleotides in length, and more preferably 2 nucleotides in length. The sequence of the loop can include nucleotide residues unrelated to the target. In one particularly preferred embodiment, the loop is 5'-UU-3'. In some embodiments it may include non-nucleotides moieties. Yet in other embodiments, the loop does not include any non-nucleotides moieties. Optionally, the shRNA can have an overhang region of 2 bases on 3' end of the molecule. The shRNA can also comprise RNAs with stem-loop structures that contain mismatches and/or bulges. The passenger strand that is homologous to the target can differ at about 0 to about 5 sites by having mismatches, insertions, or deletions of from about 1 to about 5 nucleotides, as is the case, for example, with naturally occurring microRNAs. RNAs that comprise any of the above structures can include structures where the loops comprise nucleotides, non-nucleotides, or combinations of nucleotides and non-nucleotides. Within any shRNA, preferably a plurality and more preferably all nucleotides are ribonucleotides.

In some embodiments, an shRNA described herein optionally includes at least one conjugate moiety.

The phrase "fractured shRNA", as used herein, refers to a short hairpin RNA that comprises two or more distinct strands. Such molecules can be organized in a variety of fashions (e.g., 5'-passenger-fracture-passenger-loop-guide, 5'-guide-loop-passenger-fracture-passenger) and the fracture in the molecule can comprise a nick, a nick bordered by one or more unpaired nucleotides, or a gap.

The phrase "T-shaped RNA" as used herein, refers to a T-shaped RNA that comprises at least three separate strands: a first strand, a second strand and a third strand. The first and second strands both comprise two regions (I and II) as follows: the first region of the first strand is capable annealing or hybridizing with the first region of the second strand; the first region of one of the strand can contain at least 17 bases that are complementary to a target mRNA; the first region of both strands can be about 17 to 29 nucleotides in length and preferably 22 nucleotides in length; the second region of the first strand can anneal or hybridize with part of the third strand; the second region of the second strand can anneal or hybridize with part of the third strand that is adjacent and 3' to the part that hybridizes with the second region of the first strand; the second regions of the first and second strands are not complementary to each other and can be about 4 to about 10 nucleotides in length, preferably 8 nucleotides in length; the third strand can be at least about 8 nucleotides in length; the third strand may have multiple sequences that are complementary to the second regions of her pairs of first and second strands so that multiple duplexes comprised of first and second strands can be annealed to the third strand; optionally, there is an overhang region of 2 bases on 3' end of the second strand.

The shRNAs, fractured shRNAs, and T-shaped RNAs described herein can be useful in implementing gene silencing. Also, they may be preferred over duplexes having lengths that are similar or equivalent to the length of the stem of the hairpin in some instances, due to the fact that the shRNAs described herein can be more efficient in RNA interference and less likely to induce cellular stress and/or toxicity.

Additionally, the phrase "short hairpin RNA" and the term "shRNA" include nucleic acids that also contain moieties other than ribonucleotide moieties, including, but not limited to, modified nucleotides, modified internucleotide linkages, non-nucleotides, deoxynucleotides and analogs of the nucleotides mentioned thereof.

The term "siRNA", as used herein, refers to an RNA molecule comprising a double stranded region and a 3' overhang of nonhomologous residues at each end. The double stranded region is typically about 18 to about 30 nucleotides in length, and the overhang may be of any length of nonhomologous residues, but a 2 nucleotide overhang is preferred.

The phrase "guide strand", as used herein, refers to a polynucleotide or region of a polynucleotide that is substantially complementary (e.g., 80% or more) or 100% complementary to a target nucleic acid of interest. The guide strand of a shRNA is also at least substantially complementary to its passenger strand. A guide strand can be composed of a polynucleotide region that is RNA, DNA or chimeric RNA/DNA. Any nucleotide within a guide strand can be modified by including substituents coupled thereto, such as in a 2' modification. The guide strand can also be modified with a diverse group of small molecules and/or conjugates. For example, a guide strand may be complementary, in whole or in part, to a molecule of messenger RNA, an RNA sequence that is not mRNA (e.g., tRNA, rRNA, hnRNA, negative and positive stranded viral RNA and its complementary RNA) or a sequence of DNA that is either coding or non-coding.

The guide strand may be part of a larger strand that comprises nucleotides other than guide strand nucleotides. For example, in the case of a T-shaped RNA structure the first or second strand can contain a guide strand and additional nucleotides that are complementary to the third strand, but not complementary to the target. In the case of a fractured hairpin, the guide strand can be part of a strand that also comprises loop region and a third region that is complementary to part of guide strand.

The phrase "passenger strand", as used herein, refers to a polynucleotide or region that has the same nucleotide sequence, in whole or in part, as a target nucleic acid such as a messenger RNA or a sequence of DNA. When a sequence is provided, by convention, unless otherwise indicated, it is the passenger strand (or region), and the presence of the complementary guide strand (or region) is implicit.

The term "complementary", as used herein, refers to the ability of polynucleotides to form base pairs with one another. Base pairs are typically formed by hydrogen bonds between nucleotide units in antiparallel polynucleotide, strands or regions. Complementary polynucleotide strands or regions can base pair in the Watson-Crick manner (e.g., A to T, A to U, C to G), or in any other manner that allows for the formation of stable duplexes.

"Perfect complementarity" or "100% complementarity", as used herein, refers to the situation in which each nucleotide unit of one polynucleotide strand or regioin can hydrogen bond with each nucleotide unit of a second polynucleotide strand or region. Less than perfect complementarity refers to the situation in which some, but not all, nucleotide units of two strands or two regions can hydrogen bond with each other. For example, for two 19-mers, if 17 base pairs on each strand or each region can hydrogen bond with each other, the polynucleotide strands exhibit 89.5% complementarity. Substantial complementarity refers to polynucleotide strands or regions exhibiting 80% or greater complementarity.

The term "deoxynucleotide", as used helrein, refers to a nucleotide or polynucleotide lacking an OH group at the 2' or 3' position of a sugar moiety with appropriate bonding and/or 2',3' terminal dideoxy, instead having a hydrogen bonded to the 2' and/or 3' carbon.

The terms "deoxyribonucleotide" and "DNA", as used herein, refer to a nucleotide or polynucleotide comprising at least one ribosyl moiety that has an H at its 2' position of a ribosyl moiety instead of an OH.

The term "mismatch", as used herein, includes situations in which Watson-Crick base pairing does not take place between a nucleotide of a guide strand and a nucleotide of a passenger strand, where the nucleotides are flanked by a duplex comprising base pairs in the 5' direction of the mismatch beginning directly after (in the 5' direction) the mismatched position and in the 3' direction of the mismatch beginning directly after (in the 3' direction) the mismatched position. Examples of mismatches include, without limitation, an A across from a G, a C across from an A, a U across from a C, an A across from an A, a G across from a G, a C across from a C, and so on. Mismatches also include an abasic residue across from a nucleotide or modified nucleotide, an acyclic residue across from a nucleotide or modified nucleotide, a gap, or an unpaired loop. In its broadest sense, a mismatch includes any alteration at a given position that decreases the thermodynamic stability at or in the vicinity of the position where the alteration appears, such that the thermodynamic stability of the duplex at the particular position is less than the thermodynamic stability of a Watson-Crick base pair at that position. Preferred mismatches include a G across from an A, and an A across from a C. A particularly preferred mismatch comprises an A across from an A, G across from a G, C across from a C, and U across from a U.

The phrase "RISC" and "RNA induced silencing complex" are used interchangeably herein, and represent a complex of proteins that mediate RNAi (see, e.g., Hutvagner, G. FEBS Letters, 2005 579(26):5850-7).

The phrase "RNA interference" and the term "RNAi" are used interchangeably herein, and refer to the process by which a single, double, or T-shaped molecule (e.g., an siRNA, an shRNA, an miRNA, a piRNA) exerts an effect on a biological process by interacting with one or more components of the RNAi pathway including, but not limited to, Drosha, DISC, Dicer, etc. The process includes, but is not limited to, gene silencing by degrading mRNA; attenuating translation, interactions with tRNA, rRNA, hnRNA, cDNA and genomic DNA; and inhibiting as well as methylating DNA with ancillary proteins. In addition, molecules that modulate RNAi (e.g., siRNA, piRNA, or miRNA inhibitors) are included in the list of molecules that enhance the RNAi pathway (see, e.g., Tomari, Y. et al. Genes Dev. 2005, 19(5):517-29).

The phrase "silencing", as used herein, means an RNAi-mediated reduction in gene expression that can be measured by any number of methods including reporter methods such as for example luciferase reporter assay, PCR-based methods, Northern blot analysis, Branched DNA, western blot analysis, and other art recognized techniques.

The term "alkyl", as used herein, refers to a hydrocarbyl moiety that can be saturated or unsaturated, and substituted or unsubstituted. It may comprise moieties that are linear, branched, cyclic and/or heterocyclic, and contain functional groups such as ethers, ketones, aldehydes, carboxylates, etc. Unless otherwise specified, alkyl groups are not cyclic, heterocyclic, or comprise functional groups.

Exemplary alkyl groups include, but are not limited to, substituted and unsubstituted groups of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicoyl and alkyl groups of higher number of carbons, as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, nad 2-ethylhexyl. The term alkyl also encompasses alkenyl groups, such as vinyl, allyl, aralkyl and alkynyl groups. Unless otherwise specified, alkyl groups are not substituted.

Substitutions within an alkyl group, when specified as present, can include any atom or group that can be tolerated in the alkyl moiety, including but not limited to halogens, sulfurs, thiols, thioethers, thioesters, amines (primary, secondary, or tertiary), amides, ethers, esters, alcohols and oxygen. The alkyl groups can by way of example also comprise modifications such as azo groups, keto groups, aldehyde groups, carboxyl groups, nitro, nitroso or nitrile groups, heterocycles such as imidazole, hydrazine or hydroxylamino groups, isocyanate or cyanate groups, and sulfur containing groups such as sulfoxide, sulfone, sulfide, and disulfide. Unless otherwise specified, alkyl groups do not comprise halogens, sulfurs, thiols, thioethers, thioesters, amines, amides, ethers, esters, alcohols, oxygen, or the modifications listed above.

Further, alkyl groups may also contain hetero substitutions, which are substitutions of carbon atoms, by for example, nitrogen, oxygen or sulfur. Heterocyclic substitutions refer to alkyl rings having one or more heteroatoms. Examples of heterocyclic moieties include but are not limited to morpholino, imidazole, and pyrrolidino. Unless otherwise specified, alkyl groups do not contain hetero substitutions or alkyl rings with one or more heteroatoms (i.e., heterocyclic substitutions).

The preferred alkyl group for a 2' modification is a methyl group with an O-linkage to the 2' carbon of a ribosyl moiety, i.e., a 2' O-alkyl that comprises a 2'-β-methyl group.

The phrase "2'-O-alkyl modified nucleotide", as used herein, refers to a nucleotide unit having a sugar moiety, for example a deoxyribosyl moiety that is modified at the 2' position such that an oxygen atom is attached both to the carbon atom located at the 2' position of the sugar and to an alkyl group. In various embodiments, the alkyl moiety consists essentially of carbons and hydrogens. A particularly preferred embodiment is one wherein the alkyl moiety is methyl.

As used herein, the term "2' carbon modification" refers to a nucleotide unit having a sugar moiety, for example a moiety that is modified at the 2' position of the sugar subunit. A "2'-O-alkyl modified nucleotide" is modified at this position such that an oxygen atom is attached both to the carbon atom located at the 2' position of the sugar and to an alkyl group, e.g., 2'-O-methyl, 2'-O-ethyl, 2'-O-propyl, 2'-O-isopropyl, butyl, 2'-O-isobutyl, 2'-O-ethyl-O-methyl(—OCH$_2$CH$_2$OCH$_3$), and 2'-O-ethyl-OH(—OCH$_2$CH$_2$OH). A "2' carbon passenger strand modification", as used herein, refers to a modification at the 2' carbon position of a nucleotide on the passenger strand. A "2' carbon guide strand modification", as used herein, refers to a modification at the 2' carbon position of a nucleotide on the guide strand.

The term "nucleotide", as used herein, refers to a ribonucleotide or a deoxyribonucleotide or modified from thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Preferably, a "nucleotide" comprises a cytosine, uracil, thymine, adenine, or guanine moiety.

Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, NH$_2$, NHR, NR$_2$, or CN, wherein R is an alkyl moiety as defined herein. Nucleotide analogs also include nucleotides with bases such as inosine, queuosine, xanthine, sugars such as 2'-methyl ribose, non-natural phophodiester linkages such as methylphosphonates, phosphorothioates and peptides.

Modified bases refer to nucleotide bases such as, for example, adenine, guanine, cytosine, thymine, and uracil, xanthine, inosine, and queuosine that have been modified by the replacement or addition of one or more atoms or groups. Some examples of types of modifications include nucleotides that are modified with respect to the base moieties, include but are not limited to, alkylated, halogenated, thiolated, aminated, amidated, or acetylated bases, in various combinations. More specific modified bases include, for example, 5-propynyluridine, 5-propynylcytidine, 6-methyladenine, 6-methylguanine, N,N,-dimethyladenine, 2-propyladenine, 2-propylguanine, 2'-aminoadenine, 1-methylinosine, 3-methyluridine, 5-methylcytidine, 5-methyluridine and other nucleotides having a modification at the 5 position, 5-(2-amino)propyluridine, 5-halocytidine, 5-halouridine, 4-acetylcytidine, 1-methyladenosine, 2-methyladenosien, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4-thioribose, and other sugars, heterocycles, or carbocycles. The term nucleotide analog also includes what are known in the art as universal bases. By way of example, universal bases include but are not limited to 3-nitropyrrole, 5-nitroindole, or nebularine.

Further, the term nucleotide analog also includes those species that have a detectable label, such as, for example, a radioactive or fluorescent moiety, or mass label attached to the nucleotide.

The term "overhang", as used herein, refers to terminal non-base pairing nucleotide(s) resulting from one strand or region extending beyond the terminus of the complementary strand to which the first strand or region forms a duplex. One or more polynucleotides that are capable of forming a duplex through hydrogen bonding can have overhangs. The single-stranded region extending beyond the 3' end of the duplex is referred to as an overhang.

The term "ribonucleotide" and the phrase "ribonucleic acid" (RNA), as used herein, refer to a modified or unmodified nucleotide or polynucleotide comprising at least one ribonucleotide unit. A ribonucleotide unit comprises an oxygen attached to the 2' position of a ribosyl moiety having a nitrogenous base attached in N-glycosidic linkage at the 1' position of a ribosyl moiety, and a moiety that either allows for linkage to another nucleotide or precludes linkage.

The phrase "pharmaceutically acceptable carrier", as used herein, means a pharmaceutically acceptable salt, solvent, suspending agent or vehicle for delivering a composition of the present disclosure to the animal or human. The carrier may be liquid, semisolid or solid, and is often synonymously used with diluent, excipient or salt. The phrase "pharmaceutically acceptable" means that an ingredient, excipient, carrier, diluent or component disclosed is one that is suitable for use with humans and/or animals without undue adverse side effects (such as toxicity, irritation, and allergic response) commensurate with a reasonable benefit/risk ratio. See Remington's Pharmaceutical Sciences 16$^{th}$ edition, Osol, A. Ed (1980).

The term "about" is used herein to mean a value±20% of a given numerical value. Thus, "about 60%" means a value of between 60±(20% of 60) (i.e., between 48 and 70).

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The disclosure illustratively described herein suitably may be practiced in the absence of any element of elements, limitation or limitations that is not specifically disclosed herein.

In some embodiments, methods of testing shRNAs targeting HCV IRES sequences are included to identify those sequences having sufficient activity (e.g., the highest activity among a selected group of such sequences) to be a candidate for use as a treatment. Testing may also include screening for shRNAs having undesirable off-target effects, IFN induction or general cytotoxic effects. Off-target effects include, without limitation, knockdown of nontargeted genes, inhibition of expression of non-targeted genes, and competition with natural microRNA pathways. Methods of identifying cytotoxic effects are known in the art.

In one embodiment, an shRNA described herein comprises a sequence complementary to a sequence of the internal ribosome entry site (IRES) element of hepatitis C virus (HCV).

A dual reporter luciferase plasmid was used in which firefly luciferase (fIluc) expression was dependent on the HCV IRES. Expression of the upstream renilla luciferase is not HCV IRES-dependent and is translated in a Cap-dependent process. Direct transfection of HCV IRES shRNAs efficiently blocked HCV IBES-mediated flue expression in human 293FT and Huh7 cells. Control shRNAs containing a double mutation had little or no effect on fLuc expression, and shRNAs containing only a single mutation showed partial inhibition. These shRNAs were also evaluated in a mouse model where DNA constructs were delivered to cells in the liver by hydrodynamic transfection via the tail vein. The dual luciferase expression plasmid, the shRNAs, and secreted alkaline phosphatase plasmid were used to transfect cells in the liver, and the animals were imaged at time points over 12 to 96 hours. In vivo imaging revealed that HCV IRES shRNA directly, or alternatively expressed from a polIII-plasmid vector, inhibited HCV IRES-dependent reporter gene expression; mutant or irrelevant shRNAs had little or no effect. These results indicate that shRNAs, delivered as RNA or expressed from viral or nonviral vectors, are useful as effective antivirals for the control of HCV and related viruses.

To further investigate the relationship between the RNAi activity and the structure of synthetic shRNA, multiple shRNAs, fractured shRNA and T-shaped RNA with the guide strand sequence complementary to a sequence of the HCV IRES and the corresponding synthetic siRNAs comprising the same sequence were assayed for inhibitory activity, IFN and cytotoxicity. Most of the tested constructs exhibited a high level of RNAi activity. In general, shRNA with guide strand at the 5' end of the hairpin was more potent than that with the same guide strand at the 3' end. Structural variants of shRNA with 5'-guide strand were then further investigated.

The size and sequence of the loop region of the shRNA was also investigated. The loop can be as small as one nucleotide without significantly affecting the shRNA activity and does not have a clear upper limit on loop size; generally, a loop is between two to ten nucleotides, and is generally a sequence that does not cause unintended effects, e.g., by being complementary to non-target gene. However, the shRNA with guide strand at the 5' end favors a short loop. Specifically, a two-nucleotide loop (5'-UU-3') provided the shRNA the best potency among the shRNAs having ten-, five-, or one-nucleotide loop. The closing base pair immediately before the loop is important to the short loop (e.g., two-nucleotide loop), but not as important to the long loop (five-nucleotide loop) in order to keep the high functionality of shRNA. Thus, shRNA with "CG clamp" immediately before UU-loop that could serve to strengthen duplex formation gave 4.6-fold lower $IC_{50}$ than that with an AU base pair (FIG. 5B). In another aspect, the loop can include the 3' part of the guide strand, directly coupled to the 5' end of the passenger strand, without affecting the gene knock-down activity of the shRNA. In this case, the loop is between two to eight nucleotides in length.

A loop structure can also include deoxyribonucleotides, non-nucleotide monomers and reversible linkages such as S—S bonds, which can be formed by oxidation of —SH groups introduced into nucleotide residues, e.g., as described in (Earnshwaw et al., J. Mol. Biol., 1997, 274:197-212; Sigurdsson et al. Thiol-containing RNA for the study of Structure and Function of Ribozymes. Methods: A Companion to Methods in Enzymology, 1999, 18:71-77).

The length of the duplex in the shRNAs also affects the target gene suppression. The shRNAs that have their passenger strand shortened from the 3' end (to 17 or 16 nucleotides in length) while the guide strand is maintained as 19-nucleotide have significantly less silencing efficacy. Shortening the passenger strand from the 5' end (to 17-nucleotide in length) while maintaining the guide strand at 19 nucleotides does not affect the shRNA activity. Interestingly, shRNA maintains some activity with passenger strands as short as 11-nucleotide in length (shortened from the 5' end) if the guide strand is maintained at 19-nucleotide in length. shRNAs that have both passenger and guide strands shortened (each 18 nucleotides in length and forming 18 base pairs in the duplex) showed very similar potency compared to the shRNA with 19-base paired duplex. Single mismatches at certain positions can be introduced into the duplex region of the shRNA without affecting their potency.

Fractured shRNA and T-shaped RNA were also tested and high levels of RNAi activity were seen, as shown in Example 6.

Whenever a range is given in the specification, for example, a temperature range, a time range, a percent sequence identity, a sequence complementarity range, a length range, or a composition or concentration range, all intermediate ranges and subranges, as well as all individual values included in the ranges given are intended to be included in the disclosure.

The invention is further illustrated by the following examples. The examples are provided for illustrative purposes only. They are not to be construed as limiting the scope or content of the invention in any way.

EXAMPLES

Example 1

Optimizing shRNA Structure to Improve Potency in Target Knockdown

To identify shRNA structures with increased potency in target knockdown, three sets of shRNAs (shRNA68, shRNA 72, shRNA 74) with 5'-passenger strand (right-hand loop) and three with 5'-guide strand (left-hand loop) were chemically synthesized by IDT (Coralvilled, Iowa), resuspended in RNase- and pyrogen-free buffer (Dharmacon) and evaluated; specifically, they were:

shRNA with the structure 5'-passenger strand-5-nt loop-guide strand-3' (SG68, SG72, and SG74)

shRNA with the structure 5'-guide strand-5-nt loop-passenger strand-3' (SG68L, SG72L, and SG74L)

The sequence of these shRNAs are shown in Table 1. shRNA loops are underlined. Nucleotides forming the 3' overhang are indicated by lower-case letters.

TABLE 1

Listing of shRNA Sequences Targeting HCV IRES

| Sequence ID# | Sequence (5'-3') | Target position on IRES | shRNA abbrev | IC$_{50}$ (pM) |
|---|---|---|---|---|
| SEQ ID NO: 1 | GCA CGA AUC CUA AAC CUG <u>ACA AUA</u> UGA GGU UUA GGA UUC GUG Cuu | 346-364 | SG68 | 235.2 |
| SEQ ID NO: 2 | UGA GGU UUA GGA UUC GUG <u>CCA AUA</u> GCA CGA AUC CUA AAC CUC Auu | 346-364 | SG68L | 8.3 |
| SEQ ID NO: 3 | GUG CAC CAU GAG CAC GAA <u>UCA AUA</u> AUU CGU GCU CAU GGU GCA Cuu | 335-353 | SG72 | 113.6 |
| SEQ ID NO: 4 | AUU CGU GCU CAU GGU GCA <u>CCA AUA</u> GUG CAC CAU GAG CAC GAA Uuu | 335-353 | SG72L | 118.9 |
| SEQ ID NO: 5 | CCU AAA CCU CM AGA AAA <u>ACA AUA</u> UUU UUC UUU GAG GUU UAG Guu | 354-372 | SG74 | 95.1 |
| SEQ ID NO: 6 | UUU UUC UUU GAG GUU UAG <u>GCA AUA</u> CCU AAA CCU CAA AGA AAA Auu | 354-372 | SG74L | 54.6 |

Human 293FT (Invitrogen) cells were maintained in DMEM with 10% heat-inactivated fetal bovine serum (Hyclone), supplemented with 2 mM L-glutamine and 1 mM sodium pyruvate. The day prior to transfection, cells were seeded at 23,000 cells per well in a 96-well plate, resulting in about 80% cell confluency at the time of transfection. Cells were transfected with Lipofectamine™ 2000 (Invitrogen, Carlsbad, Calif.) following the manufacturer's instructions. Specifically, synthetic shRNA samples with indicated concentrations (e.g., 10, 3, 1, 0.3, 0.1, 0.03, 0.01 and 0.003 nM), 13 ng DNA plasmid pSG154m (which contains an HCV IRES target sequence and a firefly luciferase reporter sequence), 20 ng pSEAP2-control plasmid (BD Biosciences Clontech, as transfection controls) were mixed with 0.25 µl Lipofectamine 2000 in OptiMem (Invitrogen) and introduced into 293FT cells in triplicate. Forty-eight hours later, the supernatant was removed, heated at 65° C. for 15-30 minutes, and 5-10 µl of the supernatant was added to 150 µl p-nitrophenyl phosphate liquid substrate system (pNPP, Sigma). After a 30-60 minute incubation at room temperature, samples were read (405 nm) on a Molecular Devices Thermomax microplate reader and quantitated using SOFTmax software (Molecular Devices). The remaining cells were lysed and luciferase activity was measured using MicroLiimat LB 96P luminometer (Berthold).

Figure 3:
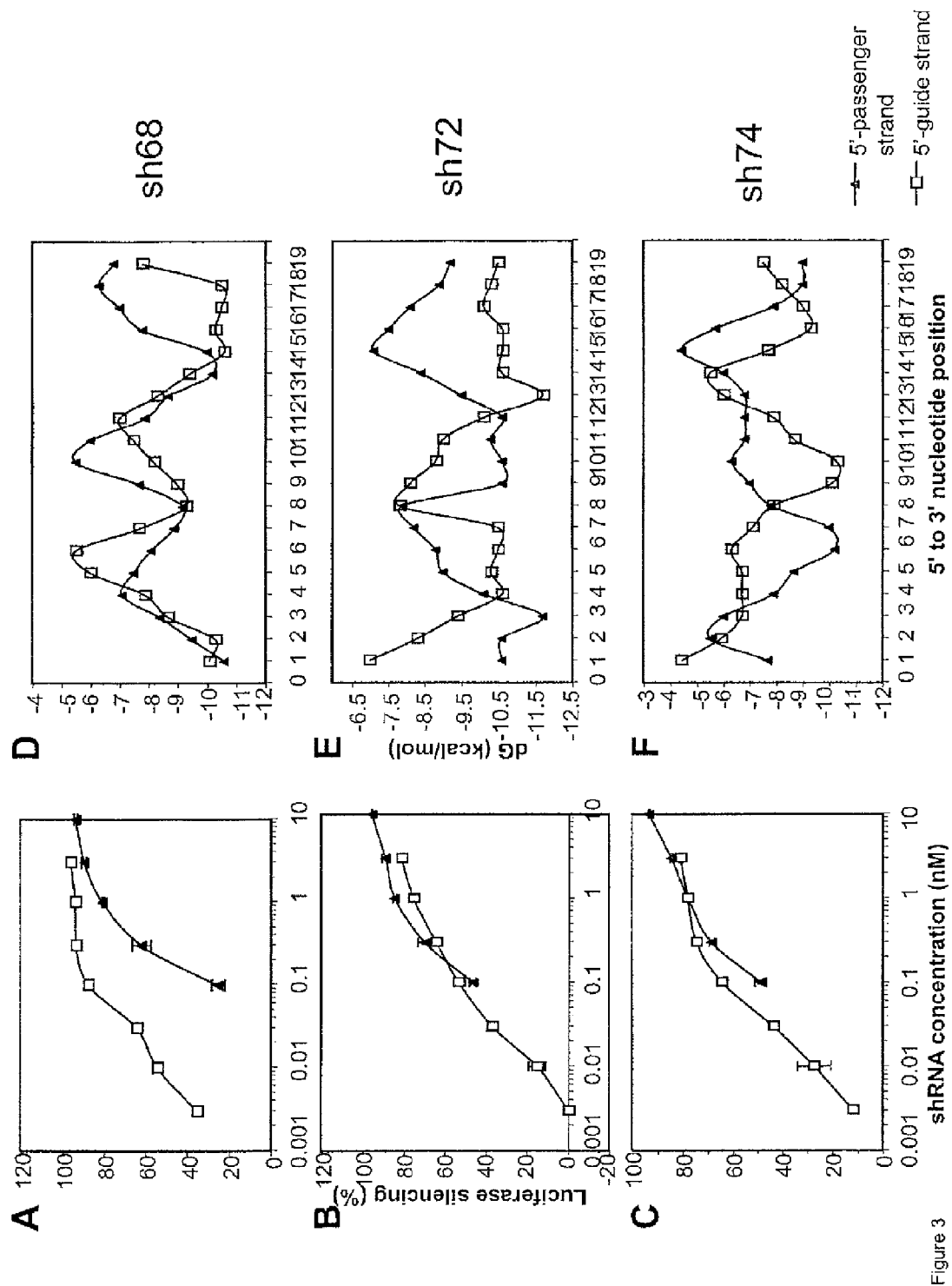
FIGS. 3A-3C compare the dose response of shRNAs having 5'-passenger strand and that having 5'-guide strand. The shRNAs were synthesized by IDT and reconstituted with siRNA buffer (Dharmacon, containing 20 mM KCl, 6 mM HEPES-KOH pH 7.5, 0.2 mM $MgCl_2$). 293FT cells (23,000 cells per well in 96-well plate) were cotransfected with shRNAs and target DNA plasmid in which firefly luciferase expression is dependent on the HCV IRES (IRES-fLuc). Lipofectamine™ 2000 (Invitrogen) was used as transfection reagent. Forty-eight hours later, the cells were lysed and firefly luciferase activity was measured by a luminometer. All data are the results of individual, independent experiments performed in triplicate.
FIGS. 3D-3F compare the same set of shRNAs for their internal stabilities calculated by Oligo 4.0. Results demonstrate that shRNAs with 5'-guide strand has enhanced functionality compared to those with 5'-passenger strand. The extent of enhancement is sequence-dependent and the differences in the internal stability of the 5' termini make an important contribution.

The results of these experiments are presented in FIG. 3A-3C. One of the three shRNAs, sh68, showed nearly a 30-fold higher potency when a left-hand (instead of right-hand) loop was used. The other two shRNAs, sh72 in particular, did not show a significant difference in potency between shRNAs with right- and left-hand loops.

To identify the key attributes associated with the potency enhancement of shRNA with 5'-guide strand, the internal stabilities of shRNAs with 5'-passenger strand and shRNAs with 5'-guide strand were calculated using the program Oligo 4.0. Only the 19 bases of the 5' strand were calculated.

The results of the calculations are presented in FIG. 3D-3F and demonstrate that the lack of activity increase in sh72 with left-hand loop were likely sequence-specific and at least partially due to the differences in the internal stability of the 5' termini. The internal stabilities of the 5' ends of shRNAs with right- and left-hand loops were very close to each other in sh68 but not in sh72. It is possible that shRNAs with left-hand loops ease the entry of, and foster the preferential use of, the guide strand since it is at the 5' end and has the 5' phosphate that is a prerequisite for binding to Dicer and Ago2 in RISC. This advantage disappears when the internal stability of the 5' ends differs significantly between shRNAs with right- and left-hand loops.

Example 2

Identifying Optimal Loop Structure and Closing Base Pair of shRNA

Figure 4:
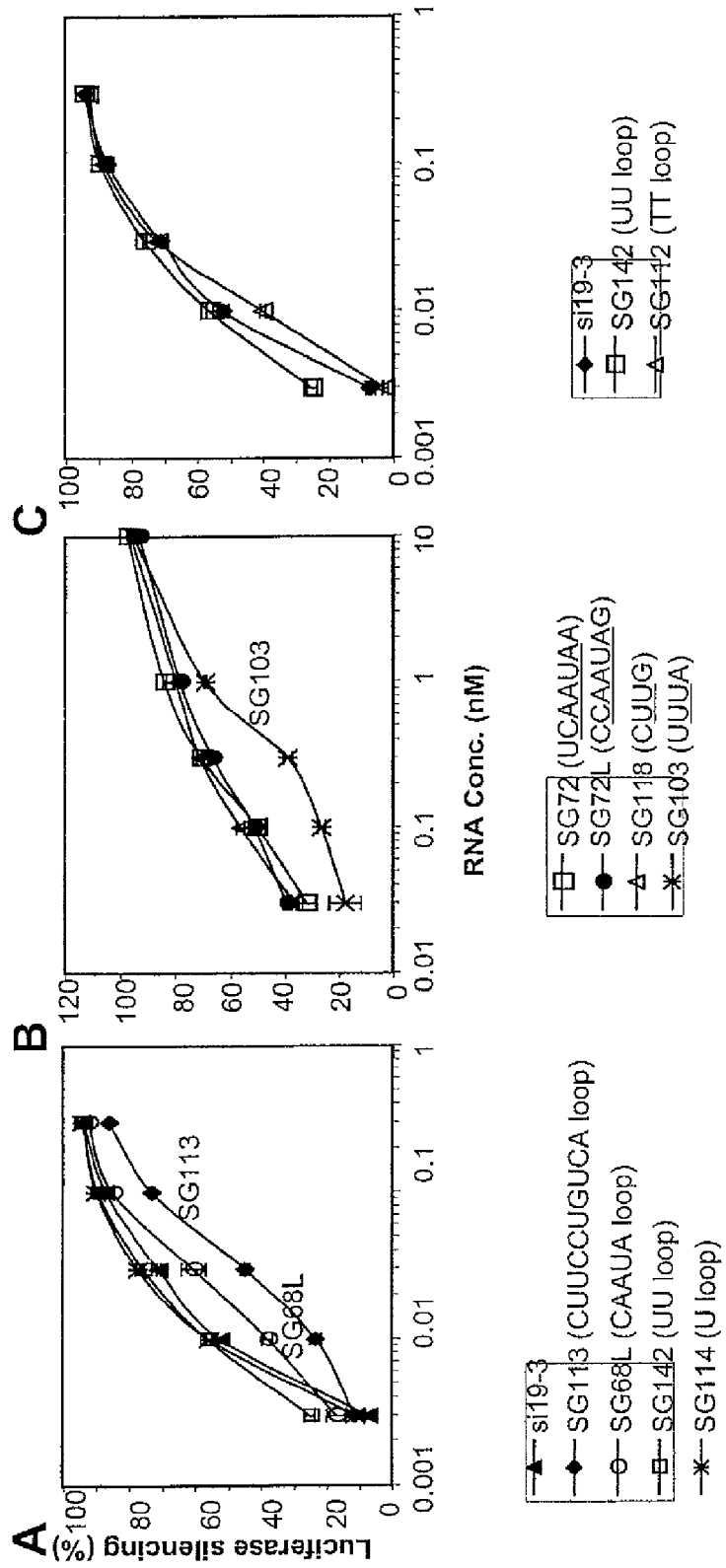
FIG. 4 depicts the dose responses of shRNAs with various loop length, sequence and closing base pairs. The experiments were done as described in FIG. 3.

The loop structure of sh19-3 was previously studied (as described in WO2007/032794, specifically incorporated by reference herein). Given the potency enhancement of SG68L versus SG68 targeting the same IRES region as sh19-3, the loop structure was re-examined. The effect of various loop structures on ability to inhibit HCV IRES-mediated reporter expression in 293FT cells was described in Example 1. The results are shown in FIG. 4. SEAP levels were uniform in all samples, indicating efficient transfection and the absence of nonspecific inhibitory or toxic effects, at shRNA concentrations of 0.003 nM to 0.3 nM.

The loop length was first investigated using shRNAs targeting the same IRES region as siRNA 19-3 (si19-3). The structure of shRNAs was 5'-guide strand-loop-passenger strand-3' (left-hand loop). The duplex length was 19-base pair with a UU-overhang at the 3' end of the passenger strand. The sequences of shRNAs with various lengths of loop are listed in Table 2. shRNA loops are underlined. Nucleotides of the 3' overhang are indicated by lower-case.

The dose response of shRNAs with a 10-nucleotide loop (SG113, 5'-CUUCCUGUCA-3') (SEQ ID NO: 41), 5-nucleotide loop (SG68L, 5'-CAAUA-3'), 2-nucleotide loop (SG142, 5'-UU-3') and 1-nucleotide loop (SG114, 5'-U-3') were examined and the results are shown in FIG. 4A. Unlike the results with shRNAs having 5'-passenger strands (right-hand loops) (Vlassov et al., Oligonucleotides 17:223-236, 2007), the shRNA with 5'-guide strands (left-hand loops) had higher potencies when the loop size was very small (1 or 2 nt) than when it was larger (5 or 10 nt; FIG. 4A). The loop sequence likely doesn't affect the shRNA activity since 3 different loop sequences were used, including one derived from a miR-23 microRNA loop structure. The IC$_{50}$ of SG142 (left-hand 5'-UU-3' loop) was as low as 4.6 pM—more potent than siRNA 19-3, which targets the same region. The shRNAs with right-hand loops have A:U as the base pair immediately adjacent to the loop, and those with left-hand loops have a C:G pair at that same position. These pairs may not in fact be base paired to relieve potential strain from a 2-nt loop. If that is the case, the C:G base pair of SG118 may participate in a tetraloop structure (CUUG) that is more stable than the 4-nt loop AUUU of SG103. Interestingly, the tetraloop-forming SG118 had the lowest IC$_{50}$ (FIG. 4B, SG118). The sequences of the duplex region are the same among these shRNAs and are listed in Table 2.

To make the loop resistant to cleavage by endoribonucleases, the 2'-deoxy dinucleotide TT was tested as the loop. No significant loss of activity (FIG. 4C) was detected upon replacement of the loop sequence UU (SG142), with TT (SG112), indicating that deoxy-substitution could be applied to the loop for ribonuclease resistance without sacrificing functional activity. It also suggests that neither Dicer nor any other endoribonuclease was involved in the processing of 19-bp shRNA, since deoxyribonucleotides cannot be cleaved by RNases, except perhaps at the 5' side of the dinucleotide.

The sequences of these shRNAs are shown in Table 2. shRNA loops are underlined. Nucleotides of the 3' overhangs are indicated by lower-case letters.

and an shRNA having a deoxyribonucleotide 3'-TT as overhang (SG111) had very similar potency to the corresponding shRNA with 3'-UU overhang.

The effect of stem length on shRNA activity was also investigated. As shown in FIG. 5B, shortening the passenger strand to 17- or 16-nt while maintaining the length of the guide strand at 19-nt significantly reduced gene silencing activity (SG115 and SG116). However, shortening both strands to 18-nt in length did not have a significant impact on potency (SG117). Surprisingly, an shRNA with a stem as short as 16-bp (SG119 with 19-nt guide strand and 17-nt passenger strand) showed similar inhibition to one having a 17-bp stem (SG117) (FIG. 5C). However, shRNAs with a stem of 15-bp (SG131) started to show reduced inhibitive activity (FIG. 6A). This indicates that high silencing activity requires a duplex length of 16-bp or higher.

To test an extreme case, the silencing by an shRNA (SG120) with an 11-bp duplex and an 8-nt loop (a 19-nt guide strand directly linked to an 11-nt passenger strand) was measured (FIG. 5C). Although the potency was lower compared

TABLE 2

Listing of shRNA Sequences with Various Loop Structure and Closing Base Pairs

| Sequence ID# | Sequence (5'-3') | Target position on IRES | shRNA abbrev | IC$_{50}$ (pM) |
|---|---|---|---|---|
| SEQ ID NO: 7 | UGA GGU UUA GGA UUC GUG CCU UCC UGU CAG CAC GAA UCC UAA ACC UCA uu | 346-364 | SG113 | 36.3 |
| SEQ ID NO: 2 | UGA GGU UUA GGA UUC GUG CCA AUA GCA CGA AUC CUA AAC CUC Auu | 346-364 | SG68L | 17.5 |
| SEQ ID NO: 8 | UGA GGU UUA GGA UUC GUG CUU GCA CGA AUC CUA AAC CUC Auu | 346-364 | SG142 | 8.7 |
| SEQ ID NO: 9 | UGA GGU UUA GGA UUC GUG CUG CAC GAA UCC UAA ACC UCA uu | 346-364 | SG114 | 10.3 |
| SEQ ID NO: 3 | GUG CAC CAU GAG CAC GAA UCA AUA AUU CGU GCU CAU GGU GCA Cuu | 335-353 | SG72 | 94.1 |
| SEQ ID NO: 4 | AUU CGU GCU CAU GGU GCA CCA AUA GUG CAC CAU GAG CAC GAA Uuu | 335-353 | SG72L | 81.3 |
| SEQ ID NO: 10 | AUU CGU GCU CAU GGU GCA CUU GUG CAC CAU GAG CAC GAA Uuu | 335-353 | SG118 | 72.7 |
| SEQ ID NO: 11 | GUG CAC CAU GAG CAC GAA UUU AUU CGU GCU CAU GGU GCA Cuu | 335-353 | SG103 | 405.4 |
| SEQ ID NO: 12 | UGA GGU UUA GGA UUC GUG CTT GCA CGA AUC CUA AAC CUC Auu | 346-364 | SG112 | 15.4 |

Example 3

Investigating the Relationship Between Efficacy and shRNA Overhang and Duplex Length Vlassov et al. found that the presence of a 3'-UU overhang increases the efficacy of 19-bp shRNAs (Vlassov, et al. 2007). The shRNAs used in this previous study had right-hand loops (5'-passenger strand-loop-guide strand-3'). Thus, the UU overhang at the 3' end of the guide strand may facilitate the binding of the Ago PAZ domain to the 3'-UU overhang of the guide strand. Since the shRNA with left-hand loop (5'-guide strand-loop-passenger strand-3') showed better target gene suppression, the effect of a UU overhang at the 3' end of the passenger strand on shRNA efficacy was examined. As shown in FIG. 5A, an shRNA lacking the 3'-UU sequence (SG105)

to the others, the short RNA hairpin still had an IC$_{50}$ of less than 200 pM. Similarly, an shRNA (SG134) with a 13-bp duplex and a 6-nt loop (a 19-nt guide strand directly linked to a 13-nt passenger strand) gave the same level of target knockdown (FIG. 6B). A further shortening of the passenger strand to 10-nt diminished the silencing significantly. Changing the 11-nt passenger strand from 3' end to 5' end of the hairpin (SG135) abolished the silencing (FIG. 6B).

Figure 5:
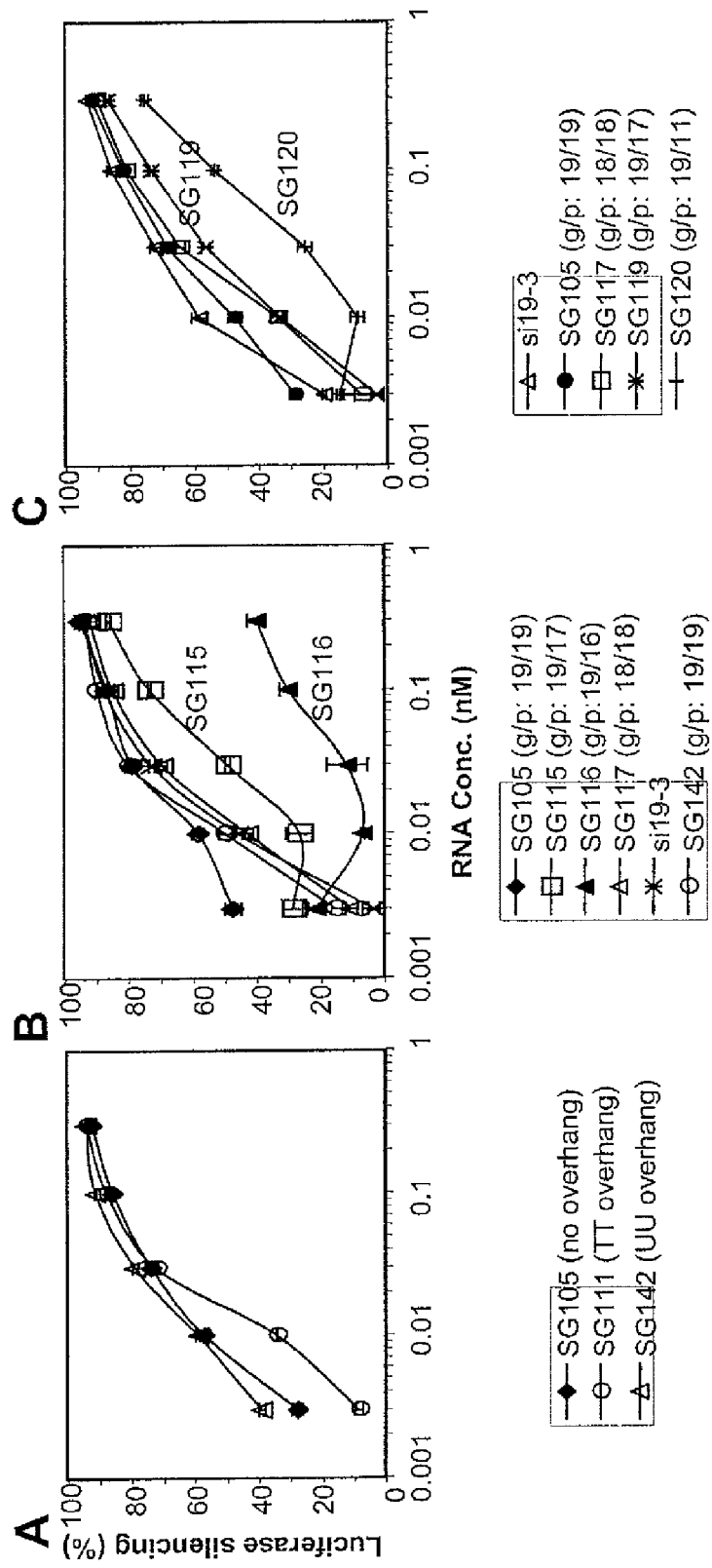
FIG. 5 depicts the dose responses of shRNAs with various duplex lengths and 3' overhangs. The experiments were done as described in FIG. 3.
Figure 6:
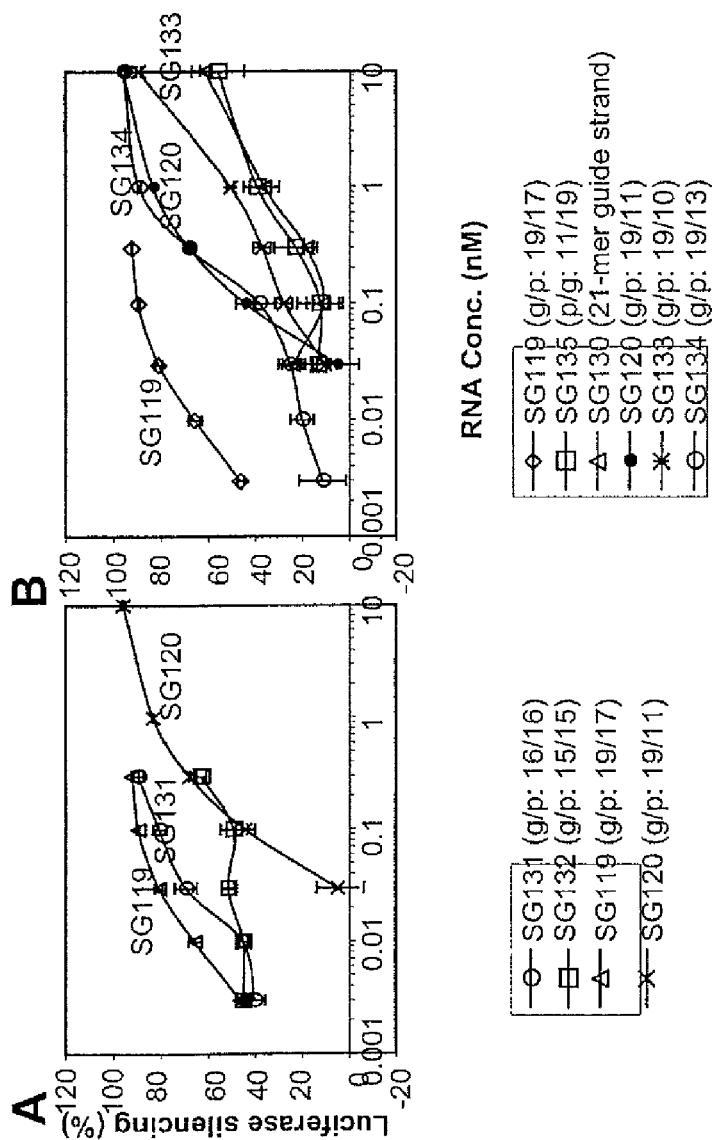
FIG. 6 depicts the dose responses of shRNAs with various short stem lengths. The experiments were done as described in FIG. 3.
Figure 7:
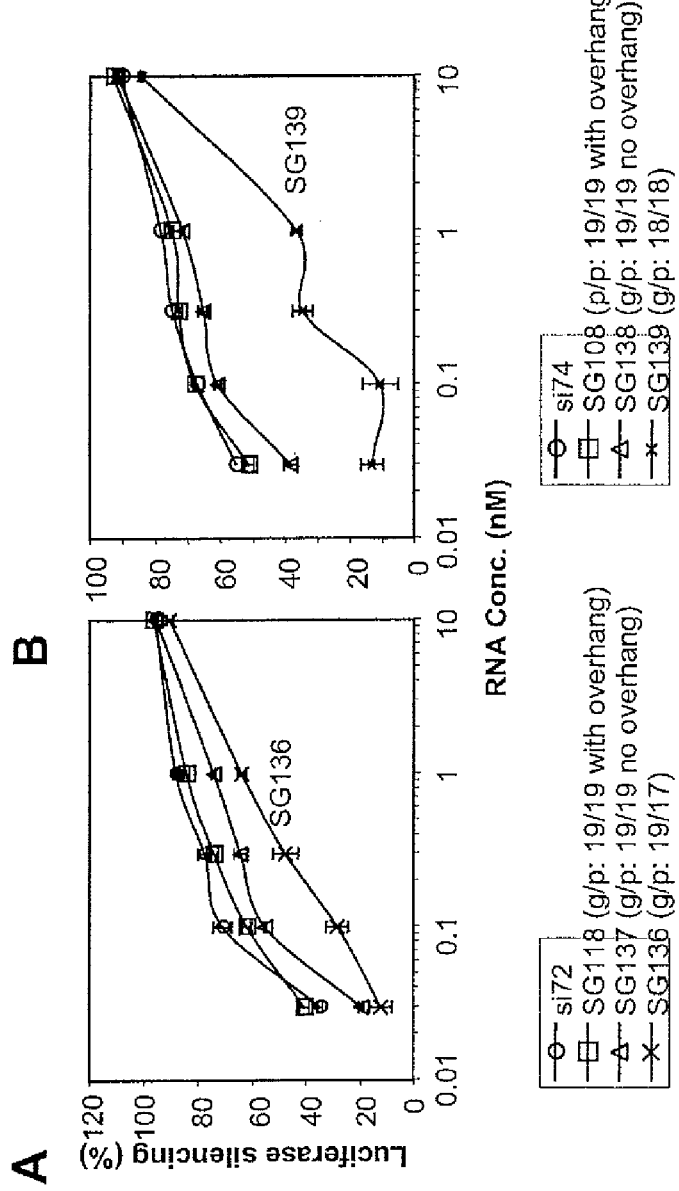
FIG. 7 depicts the potencies of various structured shRNAs against different targets. The experiments were done as described in FIG. 3.

To examine whether the overhang and stem length effects were sequence-specific, two target sequences other than the one used in FIGS. 5 and 6 were tested (FIGS. 7A and 7B). Depletion of the 3'-UU overhang did not significantly reduce the target silencing of the hairpins. Shortening the stem to 18-bp (SG139) or 16-bp (SG136) reduced the hairpins' target knock down capability, indicating this stem shortening strategy has some degree of sequence dependency.

The sequences of these shRNAs are shown in Table 3. shRNA loops are underlined. Nucleotides of the 3' overhangs are indicated by lower-case.

TABLE 3

Listing of shRNA Sequences with Various Duplex Structures

| Sequence ID NO | Sequence (5'-3') | Target position on IRES | shRNA abbrev | IC$_{50}$ (pM) |
|---|---|---|---|---|
| SEQ ID NO: 13 | UGA GGU UUA GGA UUC GUG CUU GCA CGA AUC CUA AAC CUC A | 346-364 | SG105 | 4.2-10.9 |
| SEQ ID NO: 14 | UGA GGU UUA GGA UUC GUG CUU GCA CGA AUC CUA AAC CUC Att | 346-364 | SG111 | 16.2 |
| SEQ ID NO: 8 | UGA GGU UUA GGA UUC GUG CUU GCA CGA AUC CUA AAC CUC Auu | 346-364 | SG142 | 5.7-10.6 |
| SEQ ID NO: 15 | UGA GGU UUA GGA UUC GUG CUU GCA CGA AUC CUA AAC CU | 346-364 | SG115 | 26.6 |
| SEQ ID NO: 16 | UGA GGU UUA GGA UUC GUG CUU GCA CGA AUC CUA AAC C | 346-364 | SG116 | 1007.4 |
| SEQ ID NO: 17 | UGA GGU UUA GGA UUC GUG UUC ACG AAU CCU AAA CCU CA | 346-364 | SG117 | 15-19.9 |
| SEQ ID NO: 18 | UGA GGU UUA GGA UUC GUG CAC GAA UCC UAA ACC UCA | 346-364 | SG119 | 3.7-26.8 |
| SEQ ID NO: 19 | UGA GGU UUA GGA UUC GUG CCC UAA ACC UCA | 346-364 | SG120 | 87.9-158.0 |
| SEQ ID NO: 20 | UGA GGU UUA GGA UUC GUG CUU GCA CGU AUC CUA AAC CUC Auu | 346-364 | SG110 | 7.3 |
| SEQ ID NO: 21 | UGA GGU UUA GGA UUC GUU CGA AUC CUA AAC CUC A | 346-364 | SG131 | 8.6 |
| SEQ ID NO: 22 | UGA GGU UUA GGA UUC UUG AAU CCU AAA CCU CA | 346-364 | SG132 | 26.0 |
| SEQ ID NO: 23 | UGA GGU UUA GGA UUC GUG AC UAA ACC UCA | 346-364 | SG133 | 698.3 |
| SEQ ID NO: 24 | UGA GGU UUA GGA UUC GUG CAUCC UAA ACC UCA | 346-364 | SG134 | 121.9 |
| SEQ ID NO: 25 | GCA CGA AUC CUU GAG GUU UAG GAU UCG UGC | 346-364 | SG135 | 4,863.8 |
| SEQ ID NO: 10 | AUU CGU GCU CAU GGU GCA CUU GUG CAC CAU GAG CAC GAA Uuu | 335-353 | SG118 | 51.9 |
| SEQ ID NO: 26 | AUU CGU GCU CAU GGU GCA CGC ACC AUG AGC ACG AAU | 335-353 | SG136 | 393.1 |
| SEQ ID NO: 27 | AUU CGU GCU CAU GGU GCA CUU GUG CAC CAU GAG CAC GAA U | 335-353 | SG137 | 129.0 |
| SEQ ID NO: 28 | UUU UUC UUU GAG GUU UAG GUU CCU AAA CCU CAA AGA AAA Auu | 354-372 | SG108 | 21.0 |
| SEQ ID NO: 29 | UUU UUC UUU GAG GUU UAG GUU CCU AAA CCU CAA AGA AAA A | 354-372 | SG138 | 65.9 |
| SEQ ID NO: 30 | UUU UUC UUU GAG GUU UA GUU CU AAA CCU CAA AGA AAA Auu | 354-372 | SG139 | 1,343.0 |

Example 4

Investigating the Effect of the Position and Type of Single Mismatch in 19-bp shRNA It has been shown that both guide and passenger strands of siRNA can be incorporated into RISC complex. This may be applicable to guide and passenger strands of shRNA. Since the selection of a passenger strand by Ago could induce unwanted effects if the passenger strand (the seed region in particular) were complementary to the coding region or 3'-UTR of messenger RNA, single mutations were made at positions 4 to 7 from 5' end of the passenger strand.

Figure 8:
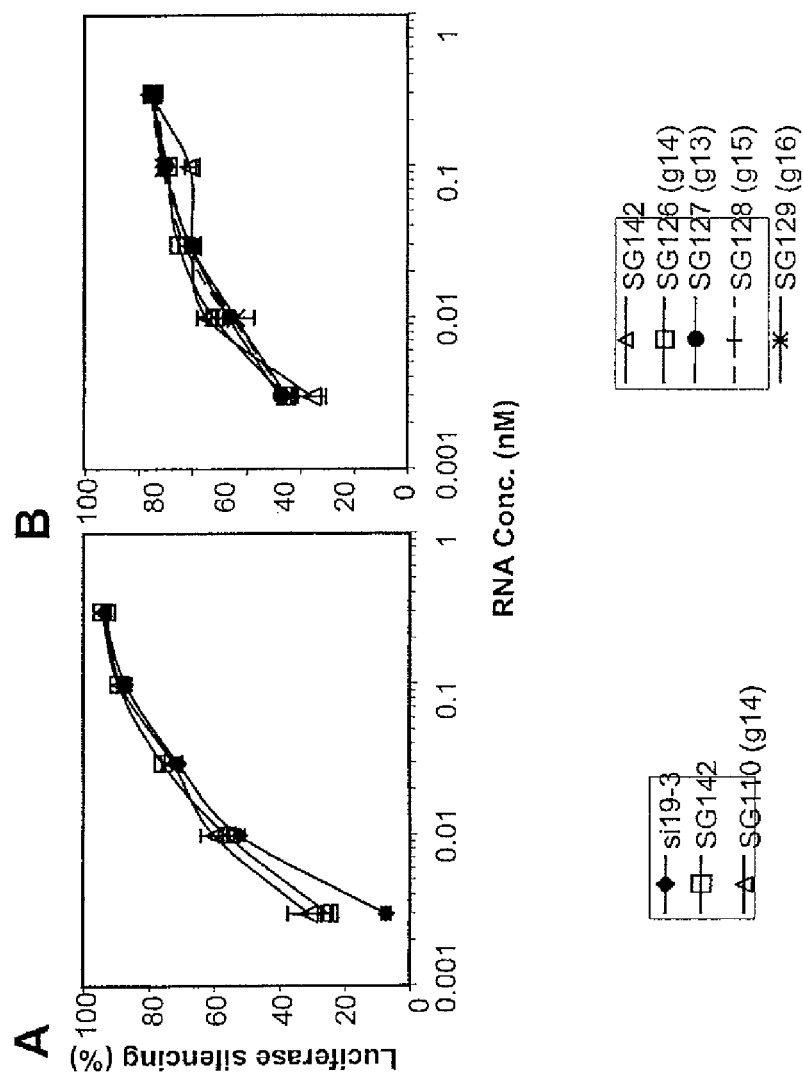
FIG. 8 depict the dose responses of shRNAs with single mismatch at different position of the duplex region.

As shown in FIGS. 8A and 8B, these mutations did not significantly affect the potency of shRNA with both strands 19-nucleotide in length, 3' UU overhang and UU-loop. In addition, this maintenance of activity with single mismatch did not appear to be unrelated to the type of mismatch (e.g., U-U (SG110)=U-C(SG126)), suggesting that this trait is sequence-independent.

The sequences of these shRNAs are shown in Table 4. shRNA loops are underlined. Nucleotides of the 3' overhangs are indicated by lower-case. Mismatched-nucleotide is indicated in italics.

TABLE 4

Listing of shRNA Sequences with Single Mismatch in the Passenger Strand

| Sequence ID NO | Sequence (5'-3') | Target position on IRES | shRNA abbrev | $IC_{50}$ (pM) |
|---|---|---|---|---|
| SEQ ID NO: 8 | UGA GGU UUA GGA UUC GUG CUU GCA CGA AUC CUA AAC CUC Auu | 346-364 | SG142 | 4.6-8.7 |
| SEQ ID NO: 20 | UGA GGU UUA GGA UUC GUG CUU GCA CG*U* AUC CUA AAC CUC Auu | 346-364 | SG110 | 7.3 |
| SEQ ID NO: 31 | UGA GGU UUA GGA UUC GUG CUU GCA CG*C* AUC CUA AAC CUC Auu | 346-364 | SG126 | 3.5 |
| SEQ ID NO: 32 | UGA GGU UUA GGA UUC GUG CUU GCA CGA *C*UC CUA AAC CUC Auu | 346-364 | SG127 | 3.5 |
| SEQ ID NO: 33 | UGA GGU UUA GGA UUC GUG CUU GCA *C*CA AUC CUA AAC CUC Auu | 346-364 | SG128 | 3.6 |
| SEQ ID NO: 34 | UGA GGU UUA GGA UUC GUG CUU GCA *G*GA AUC CUA AAC CUC Auu | 346-364 | SG129 | 4.2 |

Example 5

Investigating the Effect of Monomer and Dimer on shRNA Efficacy

Figure 9:
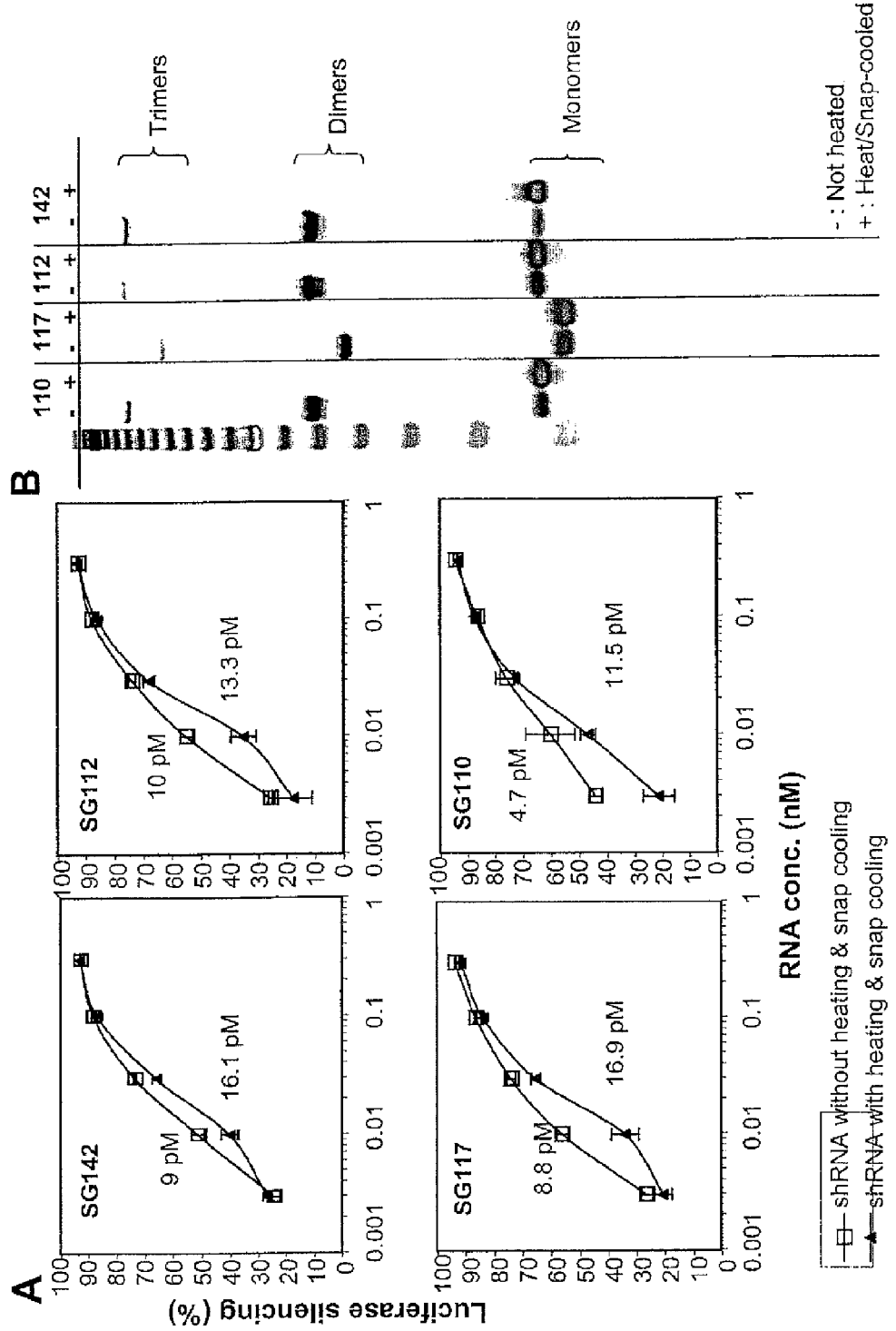
FIG. 9 depicts that the target inhibition of shRNAs are not due to dimer or oligomer formation.
Figure 10:
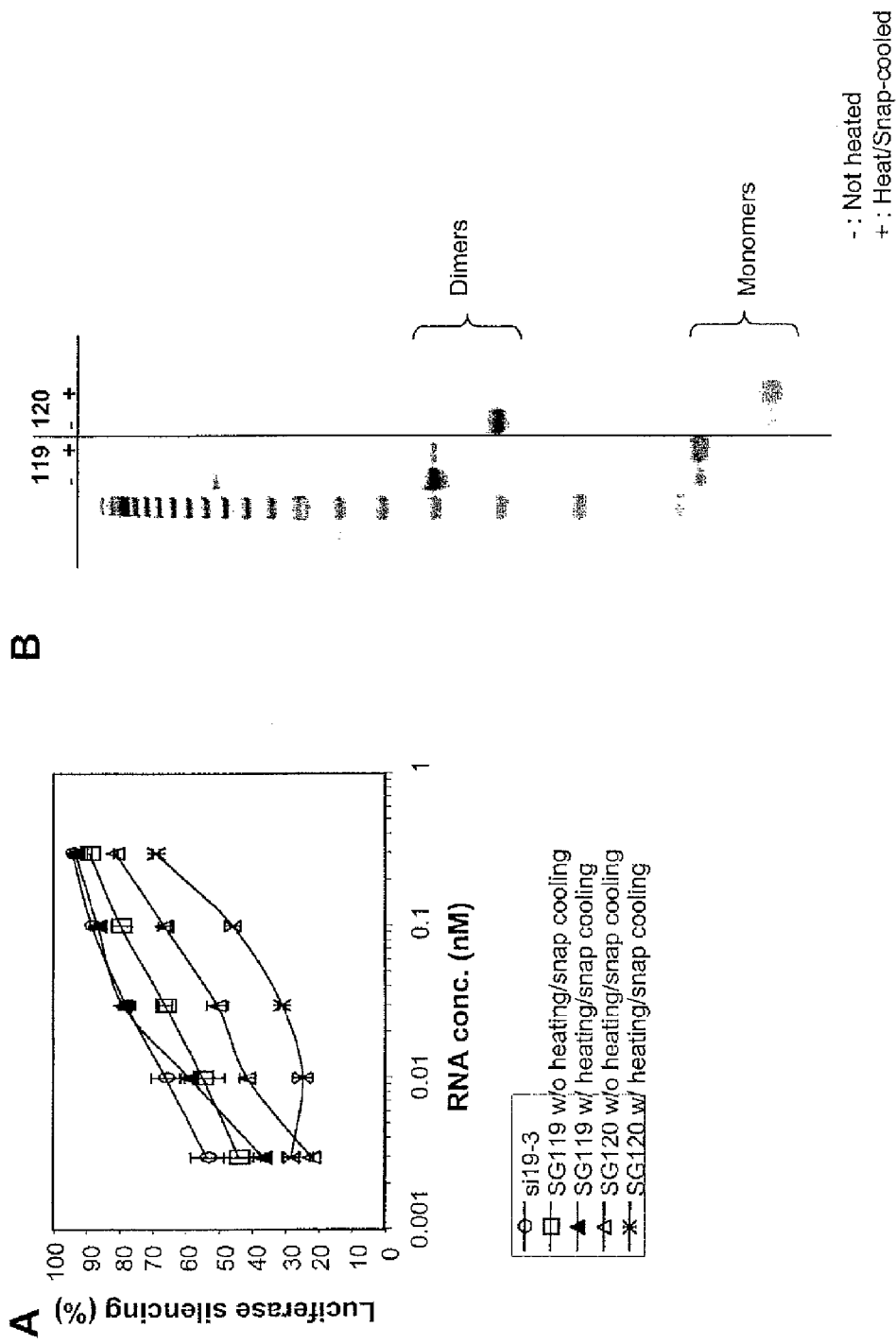
FIG. 10 depicts the different behaviors of shRNAs in monomer and mixed species.

The shRNAs synthesized and HPLC-purified by IDT were found to comprise three major species in native polyacrylamide gels: monomer, dimer and trimer. In contrast, under denaturing conditions (12% polyacrylamide gel containing 8 M urea and 20% formamide), the mixture showed only a single major band. When the shRNAs were heated to 95° C. for 4 minutes and quickly cooled in an ice bath, this mixture of monomer, dimer and trimer could be largely transformed to monomer (FIG. 9B and FIG. 10B), and monomer shRNAs remained strong inhibitors of IRES-dependent luciferase expression in 293FT cells, albeit slightly weaker than the mixture (FIG. 9A). When the shRNA was shortened to 16-nucleotide (SG119) and the dimer of this molecule formed a perfect duplex without bulge or mismatch, the monomers had better efficacy than monomer-dimer mixtures (FIG. 10A). This was probably due to the fact that dimers had an inefficient cleavage or various cleavage products by Dicer. However, when the shRNA was extremely short (11 base pairs with the rest of guide strand as loop (SG120)), the hairpin was more active in mixture, probably in dimer form, than in monomer only form (FIG. 10A). But even in pure monomer form, SG120 reduced the target gene expression with high efficiency, with $IC_{50}$ of 98.6 pM.

Example 6

Identifying Optimal shRNA Configuration with Enhanced Functionality

To identify optimal shRNA configurations that have enhanced gene knockdown, 3 shRNAs targeting the same region of IRES were synthesized and evaluated.

a. SG68L: 5'-guide strand-CAAUA (loop)-passenger strand-3' b. SG146: Annealed products from two RNA molecules. SG146-1,5'-guide strand-CAAUA (loop)-partial passenger strand-3'; SG146-2,5'-partial passenger strand that is complementary to guide strand c. SG142: 5'-guide strand-UU (loop)-passenger strand-3' shRNA samples with different concentrations (0.3, 0.1, 0.03, 0.01 and 0.003 nM) and 13 µg DNA plasmid pSG154m (containing target sequence HCV IRES and reporter sequence firefly luciferase) and pUC19 (made up the same amount of nucleic acids) were mixed with 0.25 µl Lipofectamine 2000 (Invitrogen) in OptiMem (Invitrogen) and introduced into 293FT cells (23,000 cells per well in 96-well plates). The knockdown of firefly luciferase gene expression was measured by a luminometer at 48 hrs.

Figure 11:
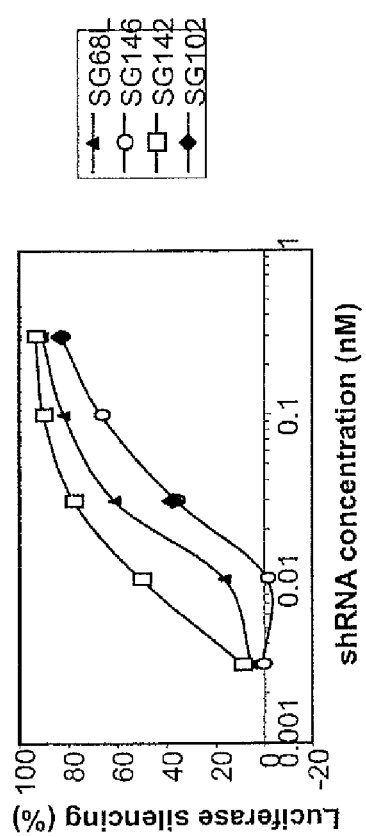
FIG. 11 depicts the potency of an shRNA with and without a nick and of a T-shaped RNA. The experiments were done as described in FIG. 3. The concentrations of shRNA used in these experiments include 0.3 nM, 0.1 nM. 0.03 nM. 0.01 nM and 0.003 nM. Only 2 concentrations (0.3 and 0.03 nM) were tested with SG102. SG68L, SG146 and SG142 have the same duplex sequence with 3'-UU overhang. SG68L and SG146 have 5'-CAAUA-3' loop whereas SG142 has 5'-UU-3' loop. SG146 is composed of two RNA molecules that were annealed together according to Dharmacon's siRNA annealing instruction. The first molecule contains guide strand, loop and 4-nucleotide passenger strand; the second molecule contains 3' end of 15-nucleotide passenger strand and 3' overhang. SG102 is composed of 3 RNA molecules (FIG. 2A) with guide and passenger strands in the first region of the first and second strands. The third strand is complementary to the second regions of the first and second strands.

The results of these experiments are presented in FIG. 11 and demonstrate: 1) shRNA with 2-nucleotide loop (SG142) was slightly more potent than shRNA with 5-nucleotide loop (SG68L); and 2) shRNA annealed from two molecules (SG146) had good knockdown functionality.

The sequences of these shRNAs are shown in Table 5. shRNA loops are underlined. Nucleotides of the 3' overhangs are indicated by lower-case.

TABLE 5

Listing of shRNA Sequences with Various Loop Structure and Closing Base Pairs

| Sequence ID# | Sequence (5'-3') | Target position on IRES | shRNA abbrev | $IC_{50}$ (pM) |
|---|---|---|---|---|
| SEQ ID NO: 2 | UGA GGU UUA GGA UUC GUG <u>CCA AUA</u> GCA CGA AUC CUA AAC CUC Auu | 346-364 | SG68L | 26.6 |
| SEQ ID NO: 8 | UGA GGU UUA GGA UUC GUG <u>CUU</u> GCA CGA AUC CUA AAC CUC Auu | 346-364 | SG142 | 11.5 |
| SEQ ID NO: 35 | UGA GGU UUA GGA UUC GUG <u>CCA AUA</u> GCA C | 346-364 | SG146-1 | 61 |
| SEQ ID NO: 36 | GAA UCC UAA ACC UCA uu | | SG146-2 | |
| SEQ ID NO: 37 | GCA CGA AUC CUA AAC CUC AAA GCA UGC UCC | 346-364 | SG102-1 | |
| SEQ ID NO: 38 | ACC GUG GUC UUU GAG GUU UAG GAU UCG UGC UU | | SG102-2 | |
| SEQ ID NO: 39 | GGA GCA UGA CCA CGG U | | SG102-3 | |

Example 7

Investigating Silencing Effect of shRNAs in Hepatoma Cell Line

Figure 12:
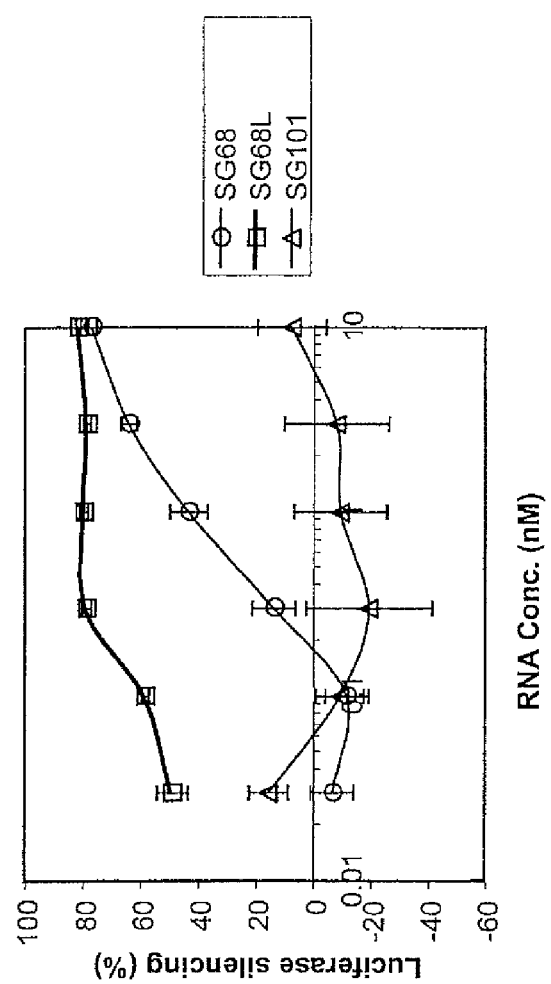
FIG. 12 depicts the potency of shRNAs in the hepatocarcinoma cell line Huh7. Consistent with the results in 293FT cells, SG68L is more potent than SG68. The negative control, SG101, did not reduce the firefly luciferase gene expression at any given concentrations.

These experiments were performed similarly to those described in Example 1, except that the cell line was changed to the hepatocarcinoma cell line Huh7 (FIG. 12). Three shRNAs with various concentrations were compared, including SG68, SG68L and negative control SG101 (sequence: 5'-CGU GCU UAG GAU UUG GAG UCA AUA ACU CCA AAU CCU AAG CAC GUU-3') (SEQ ID NO: 42). No reduction of firefly luciferase was found in cells transfected with SG101. Consistent with the results in 293FT cell, SG68L is much more potent than SG68 in silencing target gene expression in hepatocarcinoma cells.

Example 8

High Efficacy of shRNAs are not Due to IFN Response or Cytotoxicity

Some siRNAs or shRNAs induce an IFN response and/or off-target effects. To investigate whether the shRNAs tested above had these unwanted features, the IFN-responsive gene OAS1 was measured after shRNA transfection. Specifically, human PBMCs were prepared from buffy coats by density gradient centrifugation, washed, and then resuspended in RPMI 1640 containing 10% heat-inactivated fetal calf serum. The cells were cultured at $5 \times 10^5$ cells per well in 24-well plates and then transfected for 24 hours with shRNAs (20 nM, about 170 to 180 ng)/DOTAP (1.5 µl, Roche) complexes. The cells were then lysed in Trizol (Invitrogen) and total RNA was extracted according to the manufacturer's instructions. qRT-PCR was done using High-Capacity cDNA Reverse Transcription Kits, TaqMan Universal PCR Master Mix, OAS1 (Hs00242943_ml) and GAPDH (Hs99999905_ml) Taqman probe and Fast 7500 real time PCR machine (Applied Biosystem) according to the manufacturer's instructions.

Figure 13:
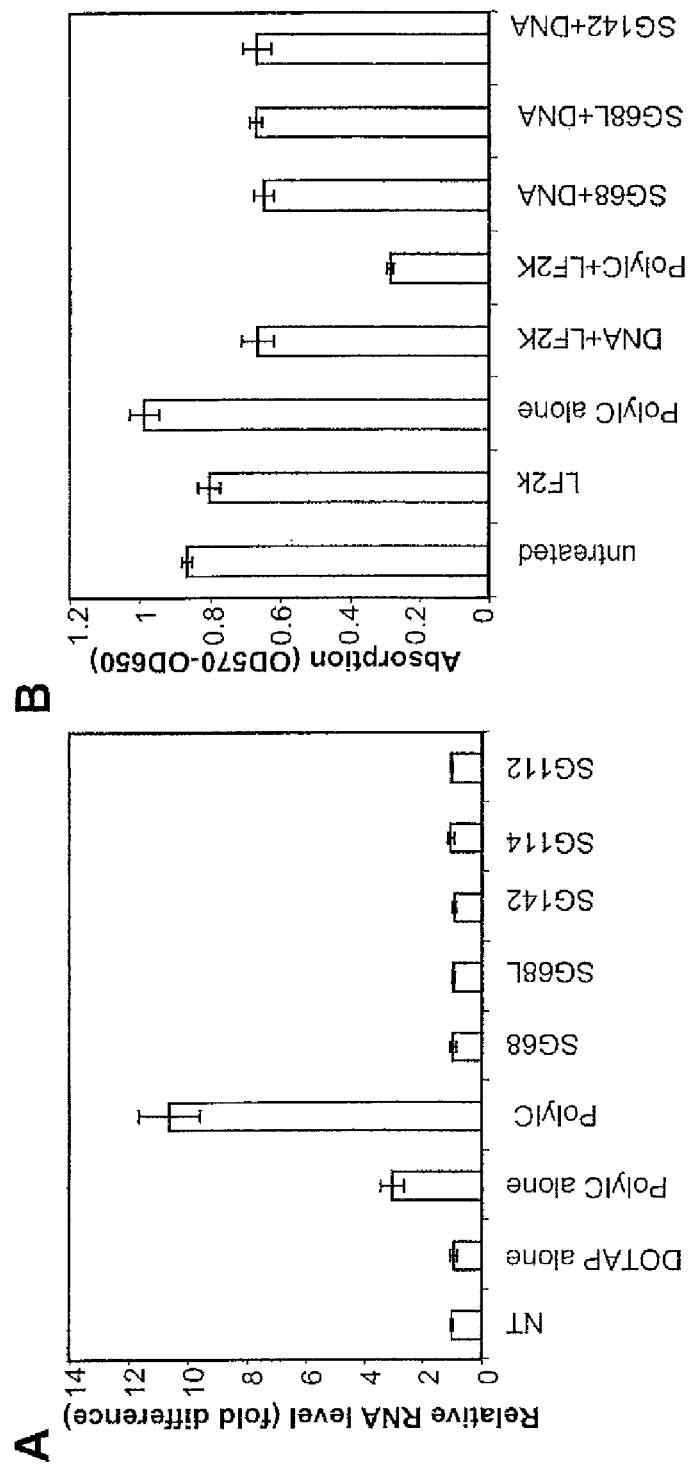
FIG. 13 shows that the inhibitory activity of several highly potent shRNAs is not due to an IFN response or cytotoxicity.

As shown in FIG. 13A, the positive control, Poly (I:C) 18 ng per well (equivalent to the amount of shRNA per well) transfected with DOTAP yielded a 10.6 fold increase of OAS1 expression compared to untreated negative control. However, none of the shRNAs tested resulted in an increase of OAS1, indicating that no IFN was induced in human PBMC.

Cytotoxicity was also tested by measuring 3-(4,5-dimethylthiazol-2-yl)-2,5-diphenyltetrazolium bromide (MTT) incorporation in human hepatocarcinoma cell line (Huh7) after shRNA transfection. Huh7 cells seeded in 96-well plate (13,000 cells/well) the night before were transfected with 10 nM shRNA together with target DNA using Lipofectamine 2000 (LF2K, Invitrogen). Poly (I:C) (33 ng) was used as positive control. 48 hours later, 16 ul/well of MTT (Sigma) in Hepes-buffered saline at 5 mg/ml was added to the culture. The cells were further incubated for 3 hours before being lysed with acidic isopropanol (0.04N HCl). The dissolved formazan level was measured by a Molecular Devices Thermomax microplate reader and quantitated using SOFTmax software (Molecular Devices) with a test wavelength of 570 nm and a reference wavelength of 650 nm.

As shown in FIG. 13B, no significant cell death relative to the negative control, plasmid DNA in lipofectamine, was found. The positive control, poly(I:C) in lipofectamine, induced more than 50% cell death. Overall, the shRNAs tested above showed no IFN and no significant cytotoxicity in human PBMC and hepatocarcinoma cells.

Example 9 shRNAs with Duplex Length of 19 Base Pairs or Less are not Dicer Substrates

To investigate whether shRNAs with duplex lengths of 19 base pairs or less are able to be cleaved by Dicer, several shRNAs were selected for in vitro Dicer cleavage analysis. An shRNA (sh1) with duplex length of 25 base pairs (5'-GGGAGCACGAAUCCUAAACCUCAAA-GACUUCCUGUCAUCUUUGAGGUUUA GGA-UUCGUGCUCUU-3') (SEQ ID NO:40) was used as positive control. Specifically, all synthetic shRNAs were dissolved to 5 µM final concentration in buffer containing 20 mM KCl, 6 mM HEPES-KOH (pH 7.5), 0.2 mM $MgCl_2$. To ensure that all molecules formed hairpin monomers, shRNAs were heated to 95° C. for 4 min and then were transferred immediately to an ice-water bath to cool for ~10-20 min before further use. 8 pmol of each shRNA was incubated in a 10 μL reaction in the presence of 1 U of recombinant dicer enzyme (Stratagene, Catalog #240100) and 1× buffer containing 150 mM NaCl, 20 mM Tris-HCl (pH 8), and 2.5 mM MgCl$_2$ for 18 hours at 37° C. Control reactions that contained each shRNA but lacked dicer enzyme were incubated in parallel.

Figure 14:
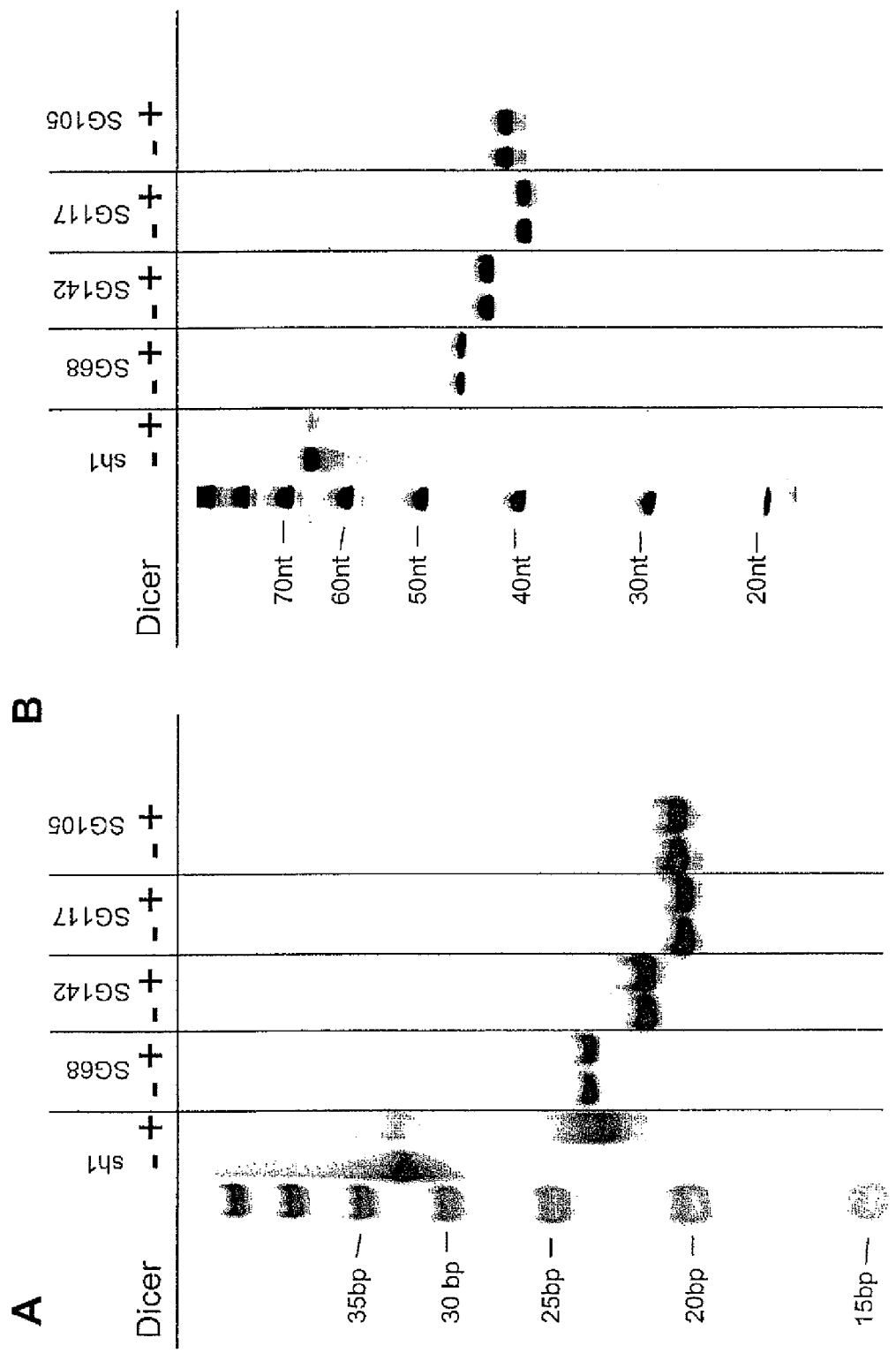
FIG. 14 shows that shRNAs with stem lengths of 19 or fewer base pairs are substrates for recombinant Dicer. The products of treatment by Dicer are analyzed by non-denaturing (FIG. 14A) and denaturing (FIG. 14B) PAGE.

Samples were analyzed by both 10% non-denaturing PAGE (FIG. 14A) and 12% denaturing PAGE (8M urea/20% formamide) (FIG. 14B) and were stained with SYBR Gold (Invitrogen). As shown in FIG. 14, the sh1 RNA that contained a duplex of 25 base pairs in length, a 10-nucleotide loop and 5'- and 3'-overhangs was cleaved by Dicer to generate a product with a size between 20 to 25 base pairs. All other shRNAs tested, including three with a stem of 19 base pairs and a hairpin of 2 or 5 nucleotides in lengths and one with a stem of 18 base pairs and a hairpin of 2 nucleotides, did not show any cleavage products in both non-denaturing and denaturing PAGEs. These results indicate that short hairpins with a duplex length of 19 base pairs or less are not Dicer substrates.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An shRNA molecule comprising:
   a. a first RNA sequence consisting of 15 nucleotides to 19 nucleotides, wherein the first sequence is at least partially complementary to a target nucleotide sequence; and
   b. a second RNA sequence consisting of 10 nucleotides to 18 nucleotides, wherein the second sequence is at least partially complementary to at least a portion of the first sequence,
   wherein:
   i. the first RNA sequence and the second RNA sequence are directly connected; or
   ii. the first RNA sequence and the second RNA sequence are connected by a loop sequence and the loop sequence consists of 1 to 2 nucleotides;
   and wherein the shRNA molecule is not a substrate of Dicer.

2. The shRNA molecule of claim 1, wherein the first RNA sequence consists of 17 nucleotides to 19 nucleotides.

3. The shRNA molecule of claim 1, wherein the second RNA sequence consists of 16 nucleotides to 18 nucleotides.

4. The shRNA molecule of claim 1, wherein the first RNA sequence and the second RNA sequence consists of the same number of nucleotides.

5. The shRNA molecule of claim 1, wherein the second RNA sequence consists of at least 1 fewer nucleotide than the first RNA sequence.

6. The shRNA molecule of claim 1, wherein
   a. the first RNA sequence consists of 18-19 nucleotides;
   b. the second RNA sequence consists of 17-18 nucleotides; and
   c. the loop sequence consists of 2 nucleotides.

7. The shRNA molecule of claim 1, wherein
   a. the first RNA sequence consists of 19 nucleotides;
   b. the second RNA sequence consists of 19 nucleotides; and
   c. the loop sequence consists of 1 nucleotide.

8. The shRNA molecule of claim 1, wherein the loop sequence consists of 2 nucleotides.

9. The shRNA molecule of claim 8, wherein the 2 nucleotides are UU.

10. The shRNA molecule of claim 1, wherein the first RNA sequence is 5' to the second RNA sequence.

11. The shRNA molecule of claim 10, wherein the RNA molecule comprises a 3' overhang.

12. The shRNA molecule of claim 1, wherein the first RNA sequence is 3' to the second RNA sequence.

13. The shRNA molecule of claim 1, wherein the second RNA sequence comprises a sequence that is at least 85% complementary to the portion of the first RNA sequence.

14. The shRNA molecule of claim 1, wherein the target nucleotide sequence is a viral sequence.

15. The shRNA molecule of claim 1, wherein the target nucleotide sequence is a hepatitis C viral sequence.

16. The shRNA molecule of claim 1, wherein the target nucleotide sequence is a hepatitis C viral sequence within the internal ribosome entry site (IRES) sequence of the hepatitis C virus.

17. A DNA sequence comprising a sequence encoding the shRNA of claim 1.

18. An RNA molecule comprising:
  a. a first RNA sequence consisting of 15 nucleotides to 19 nucleotides, wherein the first sequence is at least partially complementary to a target nucleotide sequence;
  b. a second RNA sequence consisting of 10 nucleotides to 18 nucleotides, wherein the second sequence is at least partially complementary to at least a portion of the first sequence; and
  c. a loop sequence consisting of 2 nucleotides, wherein the 2 nucleotides are UU, wherein the RNA molecule is not a substrate of Dicer.

* * * * *